US009333243B2

(12) United States Patent
Burke

(10) Patent No.: US 9,333,243 B2
(45) Date of Patent: May 10, 2016

(54) GENE DELIVERY VEHICLES IN THE TREATMENT OF NEURODEGENERATIVE DISEASES

(71) Applicant: Robert E Burke, Tenafly, NJ (US)

(72) Inventor: Robert E Burke, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/029,786

(22) Filed: Sep. 17, 2013

(65) Prior Publication Data

US 2014/0100265 A1  Apr. 10, 2014

Related U.S. Application Data

(60) Provisional application No. 61/702,184, filed on Sep. 17, 2012.

(51) Int. Cl.
*A61K 38/45* (2006.01)
*A61K 9/00* (2006.01)
*A61K 48/00* (2006.01)

(52) U.S. Cl.
CPC .............. *A61K 38/45* (2013.01); *A61K 9/0085* (2013.01); *A61K 48/005* (2013.01); *A61K 48/0075* (2013.01); *C12Y 207/11001* (2013.01); *C12N 2750/14143* (2013.01)

(58) Field of Classification Search
CPC ..................................................... A61K 38/45
See application file for complete search history.

(56) References Cited

U.S. PATENT DOCUMENTS 7,955,595 B2 * 6/2011 During et al. ................. 424/93.2

OTHER PUBLICATIONS

BD BaculoGold Technical Data Sheet for pAcGHLT-A,B,C Baculovirus Transfer Vector Set, retrieved May 2015, pp. 1-3.*
X. Chen et al., "Antiapoptotic and trophic effects of dominant-negative forms of dual leucine zipper kinase in dopamine neurons of . . . ", "Journal of Neuroscience", 2008, pp. 672-680, vol. 28, No. 3, Publisher: The Society for Neuroscience, Published in: http://www.jneurosci.org/content/28/3/672.full.pdf+html.
H. C. Cheng and R. E. Burke, "The Wld(S) mutation delays anterograde, but not retrograde, axonal degeneration of the dopaminergic nigro-striatal path", "Journal of Neurochemistry", 2010, pp. 683-691, vol. 113, No. 3, Publisher: John Wiley & Sons, Inc., Published in: http://onlinelibrary.wiley.com/doi/10.1111/j.1471-4159.2010.06632.x/pdf.
Hsiao-Chun Cheng et al., "Akt suppresses retrograde degeneration of dopaminergic axons by inhibition of macroautophagy", "Journal of Neuroscience", 2011, pp. 2125-2135, vol. 31, No. 6, Publisher: Society for Neuroscience, Published in: http://www.jneurosci.org/content/31/6/2125.full.pdf+html.

N. Kholodilov et al., "Regulation of the development of mesencephalic dopaminergic systems by the selective expression of glial cell . . . ", "Journal of Neuroscience", 2004, pp. 3136-3146, vol. 24, Publisher: The Society for Neuroscience, Published in: http://www.jneurosci.org/content/24/12/3136.full.pdf+html?sid=1869787b-920f-4bf3-8c75-f9254f49e2c3.
Kim, Sang Ryon et al., "Dopaminergic Pathway Reconstruction by Akt/Rheb-Induced Axon Regeneration", "Annals of Neurology", 2011, pp. 1-23, Publisher: American Neurological Association.
Kim, San Ryong, "AAV Transduction of Dopamine Neurons With Constitutively Active Rheb Protects From Neurodegeneration and Mediates Axon R", "Molecular Therapy", 2012, pp. 275-286, vol. 20, No. 2, Publisher: The American Soceity of Gene & Cell Therapy.
Ying-Hua Li, "Rheb and mTor Regulation Neuronal Polarity through Rap1b", "Journal of Biological Chemistry", Nov. 28, 2008, pp. 33784-33792, vol. 283, No. 48, Publisher: ASBMB, Published in: http://www.jbc.org.
Yanping Li et al., "Mutant LRRK2(R1441G) BAC transgenic mice recapitulate cardinal features of Parkinsons disease", "Nature Neuroscience", 2009, pp. 826-828, vol. 12, No. 7, Publisher: Nature Publishing Group, Published in: http://www.nature.com/neuro/journal/v12/n7/pdf/nn.2349.pdf.
Morita, Tsuyoshi, "Specification of Neuronal Polarity Regulated by Local Translation of CRMP2 and Tau vi the mTor-p70S6K Pathway", "Journal of Biological Chemistry", Oct. 2, 2009, pp. 27734-27745, vol. 284, No. 40, Publisher: ASBMB, Published in: http://www.jbc.org.
Ries, Vincent, "Oncoportein Akt/PKB induces trophic effects in murine model of Parkinson's Disease", "PNAS", Dec. 5, 2006, pp. 18757-18762, vol. 103, No. 49, Publisher: National Academy of Sciences, Published in: http://www.pnas.org/cyi/doi/10.1073/pnas.0606501103.
Tatsuhiro Sato et al., "Characterization of the Rheb-mTOR Signaling Pathway in Mammalian Cells: Constitutive Active Mutants of Rheb and mTOR", "Methods in Enzymology", 2008, pp. 307-320, vol. 438, Publisher: Elsevier, Published in: http://www.sciencedirect.com/science/article/pii/S007668790738021X.
H. Sauer et al., "Progressive degeneration of nigrostriatal dopamine neurons following intrastriatal terminal lesions . . . ", "Neuroscience", 1994, pp. 401-415, vol. 59, No. 2, Publisher: Elsevier, Published in: http://www.sciencedirect.com/science/journal/03064522/59/2.

(Continued)

*Primary Examiner* — J. E. Angell
(74) *Attorney, Agent, or Firm* — Beusse Wolter Sanks & Maire, PLLC; Judith A. Evans

(57) ABSTRACT

Currently no therapies that provide either protection or restoration of neuronal function for adult onset neurodegenerative diseases such as Parkinson's disease exist. Many clinical efforts to provide such benefits by infusion of neurotropic factors have failed. An alternative approach such as viral construct transduction may be used to directly activate the intracellular signaling pathways that mediate neurotrophic effects and induce axon growth. Viral construct transduction of dopaminergic neurons with a constitutively active human form of the p70S6K gene—hp70S6K (CA)—was shown to induce axon regeneration from living dopaminergic cell bodies that had no living axons.

9 Claims, 14 Drawing Sheets

(56) References Cited

OTHER PUBLICATIONS

Robert M. Silva et al., "CHOP/GADD153 is a mediator of apoptotic death in substantia nigra dopamine neurons in an in vivo neurotoxin model . . . ", "Journal of Neurochemistry", 2005, pp. 974-986, vol. 95, Publisher: John Wiley & Sons, Published in: http://onlinelibrary.wiley.com/doi/10.1111/j.1471-4159.2005.03428.x/pdf.

Zhang, Wei-Guo, "Identification and Characterization of a Constitutively T-loop phosphorylated and active recombinant S6K1: Expression,", "Protein Expression & Purification", 2005, pp. 414-420, vol. 46, Publisher: Elsevier, Published in: ier.com/locate/yprep.

Roberto Zoncu et al., "mTOR: from growth signal integration to cancer, diabetes and ageing", "Nature Reviews Molecular Cell Biology", 2011, pp. 21-35, vol. 12, Publisher: Nature Publishing Group, Published in: http://www.nature.com/nrm/journal/v12/n1/full/nrm3025.html.

* cited by examiner

AAV hp70S6K(CA): Characterization

AAV hp70S6K(CA): Effects in Normal Adult Mice

MFB AXONS TH IHC:   NO EFFECT
MFB AXONS TH-GFP:   NO EFFECT

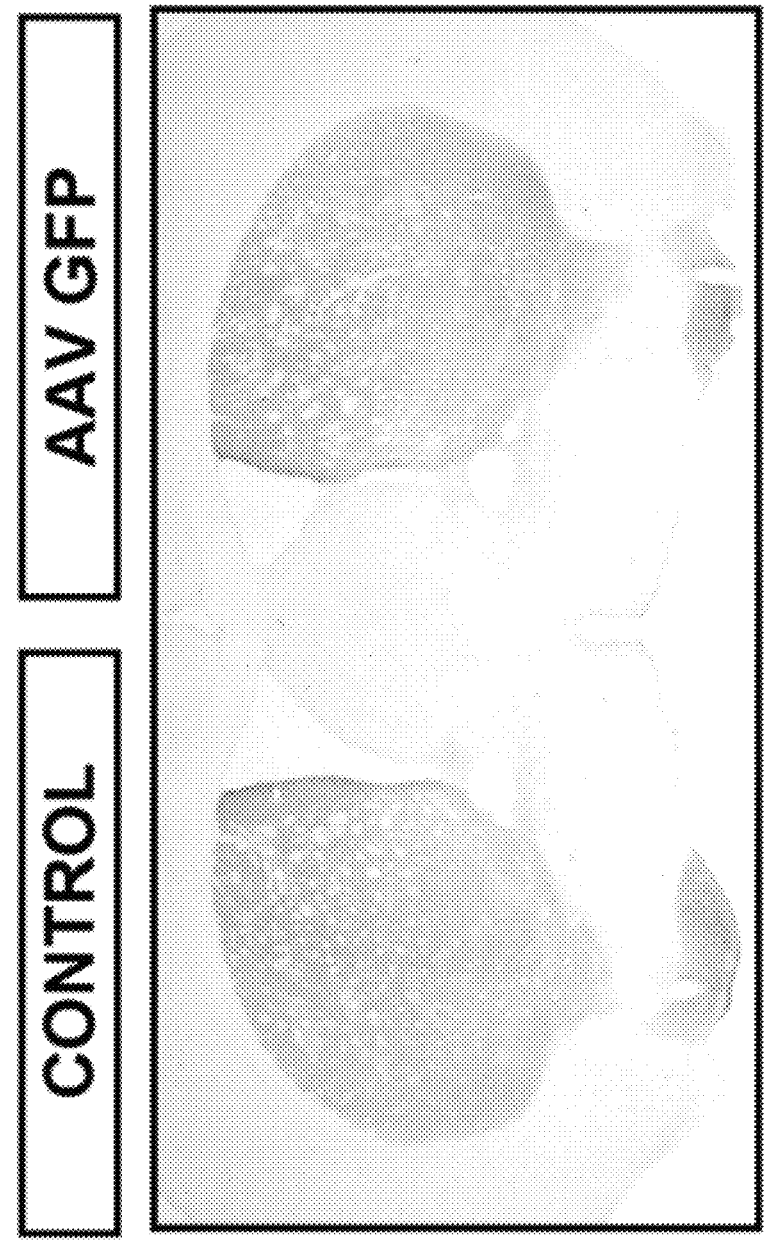

AAV hp70S6K(CA): Effects Post Intra-striatal 6OHDA
MFB: TH-POSITIVE AXONS

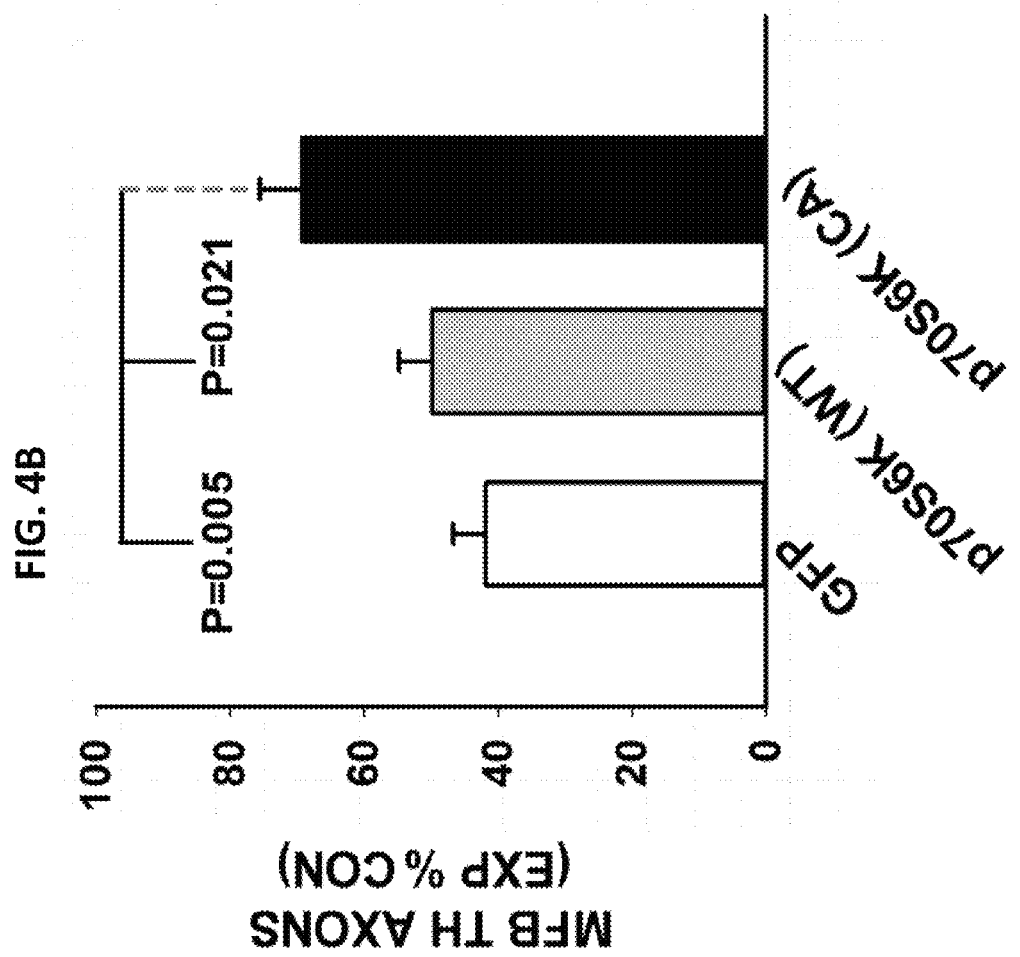

AAV hp70S6K(CA): Effects Post Intra-striatal 6OHDA
MFB: GFP - POSITIVE AXONS

AAV hp70S6K(CA): Effects Post Intra-striatal 6OHDA
MFB: TOM-TAU - POSITIVE AXONS

GENE DELIVERY VEHICLES IN THE TREATMENT OF NEURODEGENERATIVE DISEASES

CROSS-REFERENCE TO RELATED APPLICATIONS

The present application claims the benefit of Provisional Application No. 61/702,184, filed Sep. 17, 2012, the entire contents of which are hereby incorporated by reference as if fully set forth herein, under 35 U.S.C. §119(e).

STATEMENT OF GOVERNMENT INTEREST

This invention was made with Government support under Grant Nos. NS026836 and NS038370, awarded by the National Institute of Health and Grant No. W81XWH-12-1-0051, awarded by the United States Army Medical Research and Material Command. The Government has certain rights in the invention.

BACKGROUND

Parkinson's disease (PD) is a major public health problem in the world, with an estimated 1,000,000 individuals affected in the United States alone. It is a chronic, progressive, neurodegenerative disease caused by the death of neurons that produce dopamine—dopaminergic neurons—a neurotransmitter essential for proper muscle coordination, movement, and balance in the substantia nigra (SN) of the midbrain. PD symptoms vary from person to person, but the most evident symptoms include resting tremors, rigidity, slow movement, instability, stiffness, problems walking, and reduced facial expression. Other symptoms include mild to severe cognitive dysfunction and mood disorders such as depression and apathy, difficulty sleeping, loss of the sense of smell, constipation, difficulty speaking and swallowing, low blood pressure, and drooling.

Available therapies aim at replacing dopamine in the brain to restore motor function with drugs such L-Dopa. However, chronic pharmacological treatment with the dopamine precursor L-Dopa leads to a display of involuntary abnormal movements called dyskinesias in PD patients and often cognitive impairment. And there is no treatment that prevents deterioration attributable to progressive neurodegeneration. Other approaches involve infusing a protein molecule into the brain but off target effects occur that are unacceptable rendering therapeutic interventions that block or slow down the ongoing degenerative process less than successful.

Currently, no therapies exist that provide either protection or restoration of neuronal function for adult onset neurodegenerative diseases such as PD. Many clinical efforts to provide such benefits by infusion of neurotrophic factors have failed, in spite of robust effects in preclinical assessments. One important reason for these failures is the difficulty, due to diffusion limits, of providing these protein molecules in sufficient amounts to the intended cellular targets in the central nervous system. A great need exists for the development of a novel therapeutic approach that promotes an axonal regenerative response, where axons are able to regrow, reach their targets, and restore function. Gene therapy for the central nervous system is a promising approach to treat Parkinson's Disease (PD) and other central nervous system diseases, including but not limited to Alzheimer's Disease (AD) and Huntington's Disease (HD). This challenge suggests an alternative approach, that of viral construct transduction, to directly activate the intracellular signaling pathways that mediate neurotrophic effects.

SUMMARY OF THE INVENTION

The experiments described herein show that transduction of 6-OHDA-lesioned dopaminergic neurons in the substantia nigra (SN) with the adeno-associated viral construct (AAV-(hp70S6K (CA)) carrying a gene that encodes the constitutively active human form of the hp70S6K protein (hp70S6K (CA)) induced regrowth of axons from the damaged dopaminergic neurons in the SN to their target, the corpus striatum. Thus embodiments of the invention are directed to treating neurodegenerative disease by transducing neurons in degenerating areas of the CNS with a gene delivery vehicle carrying a gene encoding the constitutively active protein—(hp70S6K (CA).

An embodiment is directed to a method comprising: (a) identifying a subject that has or is at risk of developing Parkinson's disease; (b) contacting neurons in the substantia nigra in the subject with a therapeutically effective amount of a gene delivery vehicle comprising a gene hp70S6K(CA) identified by the SEQ ID NO. 1, encoding a constitutively active form of protein 70S6K (hp70S6K (delC/T389E) identified by SEQ ID NO. 2 or a biologically active form or variant thereof, in an amount that promotes axon regeneration in dopaminergic neurons of the substantia nigra, wherein the gene delivery vehicle is administered under conditions that permit transduction of the neurons with the gene delivery vehicle thereby treating the subject.

In other embodiments the substantia nigra neurons are contacted with the gene delivery vehicle by stereotaxic microinjection of the viral construct into the substantia nigra. The subject is preferably a human and the gene delivery vehicle is a viral construct.

In an embodiment the viral construct further comprise (in addition to the gene) (i) a chicken β-actin (CBA) promoter upstream from the gene; (ii) a cAPP targeting sequence; and (iii) a 3' woodchuck post-transcriptional regulatory element (WPRE (pBL)) located downstream of the hp70S6K(CA) gene identified by the SEQ ID NO. 1.

Other embodiments are directed to similar methods to treat neurodegenerative diseases generally, including Huntington's disease and Alzheimer's disease.

Some embodiments are directed to a gene delivery vehicle comprising a gene hp70S6K(CA) identified by SEQ ID NO. 1, encoding a constitutively active form of protein 70S6K (hp70S6K (delC/T389E) identified by SEQ ID NO. 2.

In some embodiments the gene delivery vehicles include a cAPP neuron targeting sequence in the gene encoding the constitutively active protein.

Some embodiments are directed to pharmaceutical compositions and kits including the gene delivery vehicles described here.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 2A reflects AAV hp70S6K (CA) expressed in a large majority of the SN dopaminergic neurons that are stained red by immunofluorescence for a marker protein, tyrosine hydroxylase (TH). hp70S6K (CA) protein has been stained green by immunofluorescence staining for FLAG epitope tag incorporated into the protein. FIG. 2B reflects the protein expressed in axons at 100× magnification. FIG. 2C shows that the mutant protein that has biologic activity as seen by induction of phosphorylation of its substrate, ribosomal protein S6.

FIG. 3A-D show the effects of AAV hp70S6K (CA) in normal adult, non-lesioned mice. The increased density of immunostaining for TH in the striatum (target of nigro-striatal projections) is most likely due to induction of sprouting of dopaminergic nerve fibers in the striatum. In normal mice, AAV hp70S6K (CA) does not induce the formation of new axons.

FIG. 4A-B show the effects of post-intra-striatal 6-OHDA. Representative horizontal sections stained for TH are shown at 15 weeks post-lesion. The red rectangles encompass the median forebrain bundle (MFB) on the lesioned side, and are shown at higher magnification n the panels at the right. AAV hp70S6K (CA) is administered at 3 weeks following a lesion of nigro-striated dopaminergic projection. Quantification of axons in the MFB as shown was performed 12 weeks after AAV injection. Significant restoration of axons projecting from the substantia nigra to the striatum is demonstrated.

Figure 1:
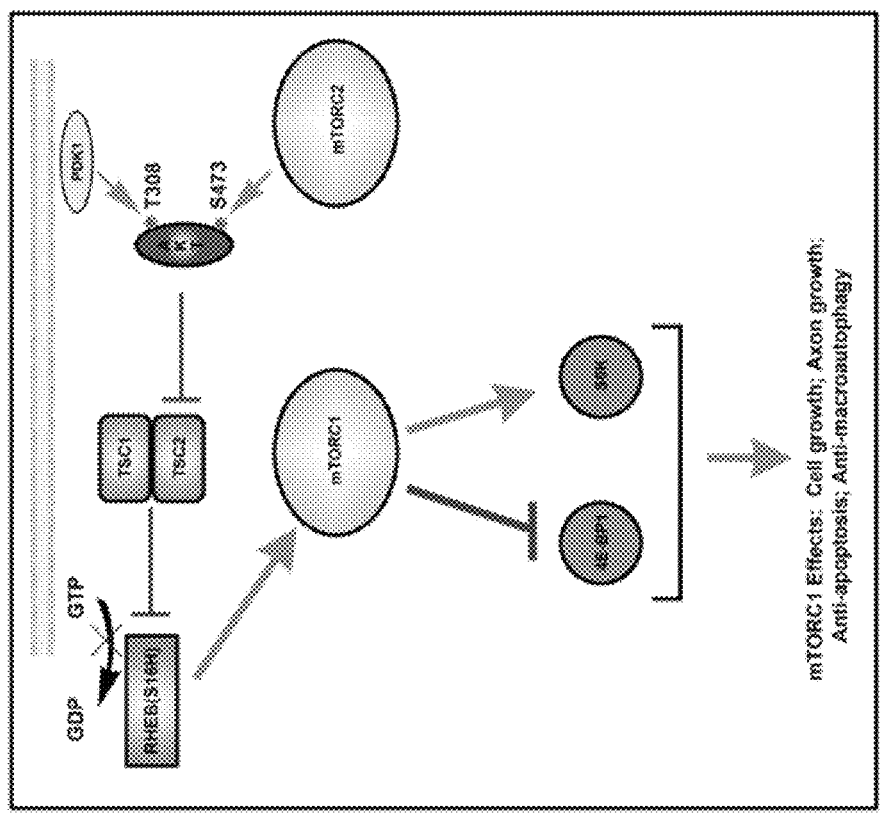
FIG. 1 is a schematic representation of the Akt-Rheb-mTor signaling pathway and identifies p70S6K as a critical downstream mediator of mTor effects. Following activation at the plasma membrane by phosphorylation by PDK1 and mTORC2, Akt phosphorylates and thereby inhibits the GTPase activity of the tuberous sclerosis complex (TSC). This inhibition allows accumulation of activated GTP-bound Rheb, which is a principal activator of the mTORC1 kinase. Two principal downstream substrates of mTORC1 are 4E-BP1 and p70S6K. Their phorphorylation mediates effects of mTORC1 activation. Constitutively active hRheb (S16H) is resistant to GTPase activation by TSC, and it therefore maintains enhanced activation of mTORC1.

In the Summary of the Invention above, in the Detailed Description of the Invention, and in the claims below, as well as the accompanying figures, reference is made to particular features of the invention. It is to be understood that the disclosure of the invention in this specification includes all possible combinations of such particular features. For example, where a particular feature is disclosed in the context of a particular embodiment or embodiment of the invention, or a particular claim, that feature can also be used, to the extent possible, in combination with and/or in the context of other particular embodiments and embodiments of the invention, and in the invention generally. For the purposes of explanation, numerous specific details are set forth in order to provide a thorough understanding of the present invention. It will be apparent, however, to one skilled in the art that the present invention may be practiced without these specific details.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

It has now been discovered that the p70S6K gene that is located downstream to Akt and hRheb encodes a p70S6K protein that possesses axon regrowth properties. The highly destructive and well-characterized 6-OHDA neurotoxin model of Parkinson Disease was used to study axon regrowth from lesioned dopaminergic cells in the Substantia Nigra (SN). Sauer H, Oertel W H. Progressive degeneration of nigrostriatal dopamine neurons following intrastriatal terminal lesions with 6 hydroxydopamine a combined retrograde tracing and immunocytochemical study in the rat. Neuroscience 1994; 59:401-415. 6-OHDA induction of retrograde degeneration of dopaminergic axons is maximal during the first week postlesion, and complete by 3 weeks. Ries V, Silva R M, Oo T F, et al. JNK2 and JNK3 combined are essential for apoptosis in dopamine neurons of the substantia nigra, but are not required for axon degeneration. J Neurochem 2008; 107: 1578-1588. Hedreen J C, Chalmers J P. Neuronal degeneration in rat brain induced by 6-hydroxydopamine; a histological and biochemical study. Brain Res 1972; 47:1-36. ANN NEUROL 2011. The experiments described herein show that transduction of 6-OHDA-lesioned dopaminergic neurons in the substantia nigra (SN) with the adeno-associated viral construct (AAV-(hp70S6K (CA)) carrying a gene that encodes the constitutively active human form of the hp70S6K protein (hp70S6K (CA)) induced regrowth of axons from the damaged dopaminergic neurons in the SN to their target, the corpus striatum. The constitutively active protein is a protein whose activity is constant. Thus embodiments of the invention are directed to treating neurodegenerative disease by transducing neurons in degenerating areas of the CNS with a gene delivery vehicle carrying a gene encoding the constitutively active protein-(hp70S6K (CA).

In order that the invention may be readily understood and put into practical effect, particular preferred embodiments will now be described by way of the following non-limiting examples.

1. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The term "constitutively active" as used herein with respect to a protein means that the protein is always active.

The term "p70S6 kinase" or "p70S6K," as used herein, means a serine/threonine kinase that acts downstream of PIP3 and phosphoinositide-dependent kinase-1 in the PI3 kinase pathway. Its target substrate is the S6 ribosomal protein. Phosphorylation of S6 induces protein synthesis at the ribosome. P70S6 kinase is in a signaling pathway that includes mTOR (the mammalian target of rapamycin). mTOR can be activated in distinct ways, thereby activating p70S6K. For example, branched chain amino acids such as leucine are sufficient to activate mTOR, resulting in an increase in p70S6K phosphorylation (thereby activating it). mTOR is also in a pathway downstream of the kinase Akt. Akt is typically activated upon stimulation of a cell with a growth factor (such as IGF-1). Akt then activates mTOR (by inhibiting the Tsc complex), leading to p70S6K activation. The Gene Bank accession number for wild type p70S6K is NM-3161.

The terms "hp70S6K (delC/T389E)" and "hp 70S6K (CA)" are used interchangeably herein to mean a constitutively active form of human p70S6K protein, in which an autoinhibitory domain at the C-terminus is deleted to activate the protein, and a threonine residue at position 389 is mutated to glutamate, hence the name hp70S6K (delC/T389E). The term "hp 70S6K (CA)" is shorthand for "hp70S6K (delC/T389E)." When the terms "hp70S6K (delC/T389E)" and "hp 70S6K (CA)" are used to describe a viral construct, the terms refer to the gene encoding the constitutively active protein, the sequence of which is set forth in SEQ ID NO: 1. The amino acid sequence for the hp 70S6K (CA) protein is set forth in SEQ ID NO: 2. It is noted that orthologs of the human protein and gene can be used in non-human animals where needed.

The terms "AAV-hp70S6K(CA)" and "AAV-hp70S6K (delC/T389E)" are used interchangeably to mean an adeno-associated viral construct that contains a gene encoding the constitutively active human form of the hp 70S6K protein. The term "hp 70S6K (CA)" is shorthand for "hp70S6K (delC/T389E)." These viral constructs also have other regulatory elements as described herein, typically the chicken β active promoter (CBA), pBL or Woodchuck post-transcriptional regulatory element (WPRE) that stimulates heterologous cDNA expression and can stimulate expression of GFP when a gene is delivered by transduction with an AAV, and a polyadenylation sequence such as (BGHpolyA) bovine growth hormone polyadenylation sequence.

The term "contacting a neuron" as used herein means that a therapeutic viral construct or other therapeutic agent makes physical contact with the targeted neuron. The viral construct or agent may be contacted with the targeted neuron in vivo for example via administration of the construct or agent to the animal such as by stereotaxic injection into the SN, or the targeted neuron may be contacted in vitro by adding the construct or agent to a culture medium, for example. Any method known in the art may be used for contacting a targeted neuron with the construct or agent, including the various delivery systems for delivering gene constructs carrying a therapeutic gene to a target. To transduce dopaminergic neurons in the SN in vivo in a subject or animal, the viral construct carrying the therapeutic gene is obtained in large quantities, is stable when administered in vivo, and will reach the targeted neurons, thereby efficiently and selectively transducing the targeted dopaminergic neurons as described. In an embodiment, the gene delivery vehicles such as viral constructs comprising the gene encoding the constitutively active hp70S6K(CA) are administered via stereotaxic microinjection. Routine experimentation can be used to optimize delivery of the viral construct/therapeutic agent to the targeted neurons.

The term "AKT" as used herein means Protein Kinase B (PKB) and is a serine/threonine-specific protein kinase that plays a key role in multiple cellular processes such as glucose metabolism, apoptosis, cell proliferation, transcription and cell migration.

The term "axon regeneration" as used herein, means the regrowth, regeneration or sprouting of new axons from a living neuron cell body.

The term "gene delivery vehicle" as used herein means a construct which is capable of delivering and, within preferred embodiments expressing, one or more gene(s) or sequence(s) of interest in a host cell. Representative examples of such vehicles include, but are not limited to, viral construct such as AAV, non-viral constructs, nucleic acid expression constructs, naked DNA, and certain eukaryotic cells (e.g., producer cells).

The term "mTor" as used herein means a mammalian target of rapamycin or as mechanistic target of rapamycin or FK506 binding protein 12-rapamycin that is associated protein 1 (FRAP1). FRAP1 is a protein which in humans is encoded by the FRAP1 gene. mTOR is a serine/threonine protein kinase that regulates cell growth, cell proliferation, cell motility, cell survival, protein synthesis, and transcription. mTOR belongs to the phosphatidylinositol 3-kinase-related kinase protein family. mTor exists as two functionally distinct complexes: (1) mTORC1 and (2) mTORC2.

The term "mTor1" or "mTOR Complex 1 (mTORC1)," as used herein, means a complex composed of mTOR, regulatory-associated protein of mTOR (Raptor), mammalian LST8/G-protein β-subunit like protein (mLST8/GβL) and the recently identified partners PRAS40 and DEPTOR. This complex is characterized by the classic features of mTOR by functioning as a nutrient/energy/redox sensor and controlling protein synthesis. The activity of this complex is stimulated by insulin, growth factors, serum, phosphatidic acid, amino acids (particularly leucine), and oxidative stress. The Rheb GTPase is a principal activator of mTORC1, that has two principal substrates: p70S6K and 4E-BP1.

The term "mTor2" or "mTOR Complex 2 (mTORC2)," as used herein, means a complex that is composed of mTOR, rapamycin-insensitive companion of mTOR (Rictor), GβL, and mammalian stress-activated protein kinase interacting protein 1 (mSIN1). mTORC2 has been shown to function as an important regulator of the cytoskeleton through its stimulation of F-actin stress fibers, paxillin, RhoA, Rac1, Cdc42, and protein kinase Cα (PKCα). mTORC2 also appears to possess the activity of a previously elusive protein known as "PDK2." mTORC2 phosphorylates the serine/threonine protein kinase Akt/PKB at a serine residue S473. Phosphorylation of the serine stimulates Akt phosphorylation at a threonine T308 residue by PDK1 and leads to full Akt activation. mTORC2 associates with the protein rictor. Its best characterized function is phosphorylation, and activation, of Akt at Ser473.

The term "neurodegenerative disease" as used herein means a disease in which neurons of the CNS die or lose function or exhibit physical degeneration including loss (death) of axons. Neurodegenerative diseases include PD, Alzheimer's disease, Huntington's disease and brain and spinal cord injuries that are associated with axon death.

The term "6-OHDA" or "6-hydroxydopamine," as used herein, means a highly destructive and well-characterized neurotoxin that induces axon death when it is injected into the intrastriatally. This neurotoxin induces retrograde degeneration of dopaminergic axons that is maximal during the first week post-lesion, and complete by three weeks. Intrastriatal injection of 6-OHDA is a model for Parkinson's Disease.

The terms "subject," "host," and "patient," as used herein, are used interchangeably and mean an animal being treated with the present compositions, including, but not limited to, simians, humans, avians, felines, canines, equines, rodents, bovines, porcines, ovines, caprines, mammalian farm animals, mammalian sport animals, and mammalian pets.

The term "single nucleotide variant" or "SNV," as used herein, means a DNA base within an established nucleotide sequence that differs from the known reference sequences. SNVs may be found within a patient sample; they may or may not be present in unperturbed populations; and they include naturally occurring single nucleotide polymorphisms, also referred to as "SNPs."

The term "single nucleotide polymorphism" or "SNP," as used herein, means a single nucleotide position in a genomic sequence for which two or more alternative alleles are present at an appreciable frequency (e.g., at least 1%) in a population of organisms.

The term "tyrosine hydroxylase" or "tyrosine 3-monooxygenase," as used herein, means the enzyme responsible for catalyzing the conversion of the amino acid L-tyrosine to L-3,4-dihydroxyphenylalanine (L-DOPA). It does so using molecular oxygen ($O_2$), as well as iron ($Fe^{2+}$) and tetrahydrobiopterin as cofactors. L-DOPA is a precursor for dopamine, which, in turn, is a precursor for the important neurotransmitters norepinephrine (noradrenaline) and epinephrine (adrenaline). Tyrosine hydroxylase catalyzes the rate limiting step in this synthesis of catecholamines. In humans, tyrosine hydroxylase is encoded by the TH gene, and the enzyme is present in the central nervous system (CNS), peripheral sympathetic neurons and the adrenal medulla. Tyrosine hydroxylase, phenylalanine hydroxylase and tryptophan hydroxylase together make up the family of aromatic amino acid hydroxylases (AAAHs).

The term "treating" as used herein means slowing, stopping or reversing the progression of a disease, particularly a neurodegenerative disease. As used herein, the terms "treatment," "treating," and the like, as used herein refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse effect attributable to the condition or disease. "Treatment," includes any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating, mitigating or ameliorating the condition or disease or symptom thereof, such as, for example, causing regression of the condition or disease or symptom thereof.

The term "transduction" as used herein means the process by which foreign DNA is introduced into a target cell via a gene delivery vehicle such as a viral construct. Transduction does not require cell-to-cell contact (which occurs in conjugation), and it is DNAase resistant (transformation is susceptible to DNAase). Transduction is a common tool used by molecular biologists to stably introduce a foreign gene into the genome of a targeted cell in the host. In this case, the gene encoding the constitutively active protein hp70S6K(CA) or a biologically active form thereof is introduced into the brain, more specifically into dopaminergic neurons in the substantia nigra (SN) using a gene delivery vehicle such as an adeno-associated virus as the viral construct. "Double transduction" can occur where SN neurons are transduced with AAV Tom-Tau simultaneously with AAV hp70S6K(CA) transduction.

The term "transgenic TH-GFP mouse" as used herein means a transgenic mouse that contains additional, artificially-introduced genetic material in every cell. This often confers a gain of function, for example the mouse may produce a new protein. A loss of function may occur if the integrated DNA interrupts another gene. The TH-GFP transgenic mouse expresses GFP in the majority of midbrain dopamine neurons under the control of the rat TH gene promoter. This transgenic mouse is useful for visualizing dopamine neurons and axons to study the physiology and pathogenesis of dopamine neurons and axons.

As used herein, "therapeutically effective amount" means an amount sufficient to treat a subject afflicted with a disease (e.g., a neurodegenerative disease) or to alleviate a symptom or a complication associated with the disease.

2. Overview

The present invention is based on the discovery that transduction of 6-OHDA-lesioned dopaminergic neurons in the SN with an adeno-associated viral construct (AAV-hp 70S6K (CA) containing a gene encoding the constitutively active form of hp70S6K protein induced axon regrowth directly from lesioned dopaminergic neuronal cell bodies in the SN projecting to the corpus striatum. In some embodiments the viral construct contained the neuron zip code cAPP that facilitates specific targeting of neurons. The protein is preferably the human protein referred herein to interchangeably as hp70S6K (delC/T389E) and hp 70S6K (CA). When the terms hp70S6K (delC/T389E) and hp 70S6K (CA) are used to describe a gene delivery vehicle such as a viral construct, they refer to the gene encoding the protein.

A longstanding belief in neuroscience has been that the mature mammalian central nervous system (CNS), unlike the peripheral nervous system (PNS), is incapable of axon regeneration (1-3). While local axon sprouting in the adult brain has been described following local administration of neurotrophic factors, long range restorative axon growth has been considered to be unachievable. The inability of the mature brain to regenerate axons has been explained by the concepts that following injury to the CNS, extrinsic factors prevent axon growth (1, 3-4), and that as the brain matures, the intrinsic developmental genetic programs that mediate axon growth are silenced. The extrinsic factors that prevent growth have been largely attributed to an unfavorable local environment following injury that is due to glial scar and inhibitory local proteins derived from damaged myelin (3).

If the intrinsic developmental genetic programs that mediate axon growth can be re-activated, it may be possible to achieve long range restorative axon growth. Such a possibility has received solid support from recent studies of the activation of Akt/mTor signaling in models of axon injury. The critical mediators of the axon growth phenotype downstream to the mTor complex have been identified (FIG. 1). Based on results with hRheb, it is now known that activation of mTor is sufficient for axon growth. MTor exists as two functionally distinct complexes (FIG. 1). mTORC1 associates with the protein raptor. The Rheb GTPase is a principal activator of mTORC1, and it, in turn, has two principal substrates: p70S6K and 4E-BP1. The second mTor complex, mTORC2, associates with the protein rictor. The function of mTORC2 is best characterized as phosphorylation and activation, of Akt at Ser473 (9-10). It was discovered that augmentation of Akt/mTor signaling resulted in substantial axon regrowth in the adult optic nerve in a crush injury model (6) and in the corticospinal tract in a spinal cord injury model (7).

Although these observations offer promise, they were made in very limited contexts. First, in these studies, the activation of Akt/mTor signaling was induced before injury. Whether beneficial effects may still be observed by activation of Akt/mTor signaling after injury, is a more realistic assessment. Second, both the optic nerve and the corticospinal tract are relatively simple, anatomically bounded projection systems. The vast majority of circuits in the CNS follow complex trajectories through a multitude of cellular environments. Whether Akt/mTor stimulation of axon growth would be able to overcome the formidable challenge of enabling new axons to "find their way" through the complex architecture of the brain was not studied. Third, in these studies the attainment of the neural target, with restoration of function, was not investigated.

It has recently been shown that fetal dopaminergic neuroblasts, when implanted into the lesioned SN of the adult brain, are capable of extending axons along the damaged nigrostriatal pathway to reach their normal target, the striatum, and achieve a functional integration into host circuitry (8). These studies suggested that injured adult nigro-striatal projections may provide a permissive environment for axon regrowth, making the dopaminergic nigrostriatal system ideal for studying this phenomenon. Due to its involvement in human Parkinson's disease, nigrostriatal neurocircuitry has been extensively studied, and it is highly characterized morphologically, neurochemically and behaviorally.

3. Background

Associated Neurodegenerative Diseases
  a. Parkinson's Disease
  Parkinson's disease (PD) is a neurodegenerative movement disorder, second only to Alzheimer's disease (AD) in prevalence (about 350 per 100,000 population.) It is clinically characterized by rigidity, slowness of movement, and tremor. Most cases of Parkinson's disease are sporadic, but both sporadic and familial forms of the disease are characterized by intracellular Lewy bodies in dying neurons of the SN, a population of midbrain neurons (~60,000) that are selectively decimated in PD. Lewy bodies are predominantly composed of alpha-synuclein. Mutations in and duplication of the gene encoding alpha-synuclein have been found in patients with familial Parkinson's disease. Another gene associated with autosomal recessive PD is parkin. Diffuse cortical Lewy bodies composed of alpha-synuclein are observed in Lewy body disease (LBD), a dementing syndrome associated with parkinsonian tone changes, hallucinations, and rapid symptom fluctuation. LBD may be the second most common form of neurodegenerative dementia after AD, accounting for 20 to 30 percent of cases among persons over the age of 60 years. Similar to the vaccine approach to Alzheimer's disease, promising results in a mouse model of Parkinson's/Lewy body disease have been obtained by immunization with alpha synuclein. Other dementing syndromes include fronto-termporal dementias, Pick's disease, and corticobasal dementia, and others known to neurological medicine.

b. Alzheimer's Disease
  Alzheimer's disease (AD) is a common dementing disordered memory and cognition neurodegenerative disease associated with brain accumulation of extracellular plaques composed predominantly of the Aβ(1-40), Aβ(1-42) and Aβ(1-43) peptides, all of which are proteolytic products of APP. In addition, neurofibrillary tangles, composed principally of abnormally phosphorylated tau protein (a neuronal microtubule-associated protein), accumulate intracellularly in dying neurons. Alzheimer's disease is marked by neuron and axon degeneration. (See, e.g., Nikolaev A, McLaughlin T, O'Leary D, Tessier-Lavigne M. APP binds DR6 to cause axon pruning and neuron death via distinct caspases. Nature. 19 Feb. 2009: 457 (7232): 981-989. doi:10.1038/nature07767. PMID 19225519.) Familial forms of AD can be caused by mutations in the APP gene, or in the presenilin 1 or 2 genes, the protein products of which are implicated in the processing of APP to Aβ. Apolipoprotein E allelic variants also influence the age at onset of both sporadic and familial forms of AD. Aβ, tau and phosphorylated tau has been detected in the blood and CSF of AD patients and in normal controls. Immunization of Alzheimer's disease patients with Aβ has shown some promising preliminary treatment results, although limited by autoimmune meningoencephalitis in humans.

Alzheimer's disease is characterized by loss of neurons in the cerebral cortex and certain subcortical regions. This loss results in gross atrophy of the affected regions, including degeneration in the temporal and parietal lobes, and parts of the frontal cortex and cingulate gyrus. Wenk G L. Neuropathologic Changes in Alzheimer's Disease. *J Clin Psychiatry.* 2003; 64 Suppl 9:7-10. Degeneration is also present in brainstem nuclei like the locus coeruleus. H, Del Tredici K. (December 2012). "Where, when, and in what form does sporadic Alzheimer's disease begin?" *Current opinion in neurology* 25 (Pt 6): 708-14. Studies using MRI and PET have documented reductions in the size of specific brain regions in people with AD as they progressed from mild cognitive impairment to Alzheimer's disease, and in comparison with similar images from healthy older adult.

c. Huntington's Disease
  Huntington's disease (HD) is an autosomal dominant, inherited, neuropsychiatric disease which gives rise to progressive motor, cognitive and behavioral symptoms. The course of Huntington's is characterized by jerking uncontrollable movement of the limbs, trunk, and face (chorea); progressive loss of mental abilities; and the development of psychiatric problems. Huntington's disease progresses without remission over 10 to 15 years and usually appears in middle age (30-50 years). Juvenile HD (also called Westphal variant or akinetic-rigid HD) develops before the age of 20, progresses rapidly, and produces muscle rigidity in which the patient moves little, if at all (akinesia). It is estimated that one in every 10,000 persons—nearly 30,000 in the United States—has Huntington's disease. Juvenile Huntington's occurs in approximately 16% of all cases. Its core pathology involves degeneration of the basal ganglia, in particular, the caudate and putamen, and is caused by an unstable expansion of the trinucleotide CAG, coding for glutamine, in a single autosomal gene IT-15 on chromosome 4, coding for a mutated form of the protein, huntingtin. How the mutation of gene IT-15 alters the function of the protein is not well understood. In Huntington's disease, synapse dysfunction is the earliest observable event, closely followed by axon degeneration often without signs of neuron loss in animal models. (See, *Current Drug Targets—CNS & Neurological Disorders*, 2004, 3, 153-160 2004 Bentham Science Publishers Ltd; and *Programmed Axon Death, Synaptic Dysfunction and the Ubiquitin Proteasome System* M. P. Coleman1 and R. R. Ribchester.)

Treatment of Huntington's disease focuses on reducing symptoms, preventing complications, and providing support and assistance to the patient. There are several substances available today for the treatment of chorea. Other neurological symptoms, such as dystonia, can be treated, but treatment is associated with a high risk of adverse events. Psychiatric symptoms, on the other hand, are often amenable to treatment and relief of these symptoms may provide significant improvement in quality of life. (Bonelli and Hofmann (2004), Expert Opin Pharmacother, 5, 767-76). Most drugs used to treat the symptoms of HD have side effects such as fatigue, restlessness, or hyperexcitability. Cystamine (Decarboxycystine) alleviates tremors and prolongs life in mice with the gene mutation for Huntington's disease (HD). The drug appears to work by increasing the activity of proteins that protect nerve cells, or neurons, from degeneration. The study suggests that a similar treatment may one day be useful in humans with HD and related disorders. (Karpuj, et al. (2002), Nat Med, 8, 143-9).

In the present specification, the invention has been described with reference to specific embodiments. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

4. Summary of Results and Embodiments of the Invention

Summary of Results

The results of the experiments described below show that transduction of 6-OHDA-lesioned neurons in the SN with an adenoviral construct (AAV-hp70S6K(CA) carrying a gene encoding the constitutively active form of p70S6K, preferably the human protein (referred to interchangeably as hp70S6K (delC/T389E) and hp 70S6K (CA)), not only preserved nigrostriatal dopaminergic axons but also induced axon regrowth directly from the lesioned dopaminergic neuronal cell body to the corpus striatum. Embodiments of the invention are directed to a new gene therapy for treating neurodegenerative diseases such as PD by transducing damaged neurons with a gene encoding the constitutively active hp70S6K (delC/T389E). The following is a summary of the results of experiments described within the Examples.

1. hp70S6K(CA) was expressed in transduced SN dopaminergic neurons that were stained red by immunofluorescence for a marker protein, tyrosine hydroxylase (TH).

2. hp70S6K(CA) protein stained green by immunofluorescence staining for the FLAG epitope tag was expressed in axons of transduced dopaminergic cells.

3. The expressed hp70S6K(CA) protein was biologically active as shown by its ability to induce of phosphorylation of ribosomal protein S6.

4. An increased density of immunostaining for TH in the striatum was observed after transduction of neurons in the SN with the AAV-hp70S6K(CA) construct due to the sprouting and regeneration of lesioned dopaminergic nerve fibers in the striatum.

5. In normal non-lesioned mice, the AAV-hp70S6K(CA) construct did not induce the formation of new axons.

6. In mice lesioned with the neurotoxin 6-OHDA, administration of the AAV-hp70S6K(CA) construct by direct SN injection caused significant restoration and regrowth of axons projecting from the SN to the striatum at 12 weeks post injection (i.e., 15 weeks post lesion).

7. Significant restoration of axons projecting from the SN to the striatum after AAV hp70S6K(CA) transduction was also observed in transgenic TH-GFP mice that were lesioned with 6-OHDA in which it was possible to visualize dopaminergic axons by the expression of GFP.

8. Restoration of axons was also revealed in 6-OHDA-lesioned SN neurons transduced simultaneously with both AAV Tom-Tau (a fluorescent fusion protein that traffics to axons) and AAV hp70S6K(CA).

Based on the experimental results described in detail in the Examples, a first set of embodiments is directed to methods of treating a subject having or at risk for Parkinson Disease, by identifying such a subject, and contacting dopaminergic neurons in the SN in the subject with a therapeutically effective amount of a viral construct comprising a gene encoding hp70S6K(CA) protein (e.g., AAV-hp70S6K(CA) or AAV-cAPP-hp70S6K(CA)) or a biologically active form or variant of hp70S6K(CA) protein in an amount that promotes axon regeneration in dopaminergic neurons of the SN and their target the corpus striatum. These methods are carried out under conditions that permit transduction of the targeted neuron with the viral construct. The subject may be human and the viral construct may be administered to the SN by stereotaxic microinjection. Any gene delivery vehicle may be used, and the non-constitutively active form of the protein may have therapeutic utility, albeit at a lower level than the constitutive form of the protein. Similar embodiments of this method for treating Alzheimer's Disease, Huntington's Disease, or other neurodegenerative diseases (e.g., brain and spinal cord injuries) associated with axon death are also described.

Another embodiment is directed to any gene delivery vehicle carrying a gene encoding hp70S6K(CA) protein. In an embodiment the gene delivery vehicle is the viral construct AAV-hp70S6K(CA) comprising a chicken β-actin (CBA) promoter; an hp70S6K(CA) gene located downstream of the chicken β-actin promoter; a 3' woodchuck post-transcriptional regulatory element (WPRE (pBL)) located downstream of the hp70S6K(CA) gene; and a BGHpolyA polyadenylation sequence inserted before the 3' ITR [inverted terminal repeat] sequence. In another embodiment the gene delivery vehicle or viral construct further contains a cAPP neuron targeting sequence. In such a construct cAPP is part of the coding sequence, placed at the N-terminus. Those of ordinary skill in the art recognize that the viral construct may also include origins of replication, regulatory sequences, selectable markers, tags, and unique restriction sites. Certain embodiments are also directed to pharmaceutical compositions and kits that comprise these gene delivery vehicles e.g., AAV-hp70S6K(CA).

The following technological details describe broadly certain aspects of preferred embodiments of the invention.

Gene Therapy

Gene therapy is the administration of a gene encoding a protein of interest as a pharmaceutical agent to treat a disease. Today, most gene therapy studies are aimed at cancer and hereditary diseases linked to a genetic defect. In the present embodiments, a gene encoding the constitutively active protein hp70S6K(CA) or a biologically active form or variant thereof is transduced into targeted neurons to induce axon regrowth from damaged neurons. A defective gene is not being replaced. The most common form of gene therapy involves transducing targeted cells in the host with DNA that encodes a functional, therapeutic gene, in this case the gene is one that encodes the protein hp70S6K(CA) that induces axon regrowth from damaged neurons, specifically in PD or another of the enumerated diseases. In the present embodiments of gene therapy, the gene is packaged within a "viral construct" under such conditions that facilitates the transfer the gene to the targeted neurons. Once inside the neuron, the DNA is expressed by the cell machinery, resulting in the production of the constitutively active hp70S6K (CA) protein, which in turn treats the patient's neurodegenerative disease. In the case of PD, the viral construct is administered specifically to dopaminergic neurons in the SN. Delivery of DNA into cells can be accomplished by a number of methods, summarized below.

Types of Viral Constructs Used in Gene Therapy

According to the various embodiments of the present invention, a variety of known nucleic acid viral constructs may be used to deliver the hp706K(CA) gene to the targeted neurons, e.g., recombinant viruses, such as recombinant adeno-associated virus (AAV), recombinant adenoviruses, recombinant retroviruses, recombinant poxviruses, and other known viruses in the art, as well as plasmids, cosmids, and phages. Options for gene delivery viral constructs are well known (see, e.g., Ausubel et al., Current Protocols in Molecular Biology, John Wiley & Sons, New York, 1989; Kay, M. A., et al., 2001 Nat. Medic., 7(1):33-40; and Walther W. and Stein U., 2000 Drugs, 60(2): 249-71). Methods for assembly of the recombinant viral constructs are well-known (see, e.g., International Patent Publication No. WO 00/15822, published Mar. 23, 2000 and other references cited herein).

Viral constructs for delivering nucleic acids can be viral, non-viral, or physical. (See, e.g., Rosenberg et al., Science, 242:1575-1578 (1988), and Wolff et al., Proc. Natl. Acad. Sci. USA 86:9011-9014 (1989)). Discussion of methods and compositions for use in gene therapy include Eck et al., in Goodman & Gilman's The Pharmacological Basis of Therapeutics, Ninth Edition, Hardman et al. eds., McGray-Hill, New York, (1996), Chapter 5, pp. 77-101; Wilson, Clin. Exp. Immunol. 107 (Suppl. 1):31-32 (1997); Wivel et al., Hematology/Oncology Clinics of North America, Gene Therapy, S. L. Eck, ed., 12(3):483-501 (1998); Romano et al., Stem Cells, 18:19-39 (2000), and the references cited therein. U.S. Pat. No. 6,080,728 also provides a discussion of a wide variety of gene delivery methods and compositions. The routes of delivery include, for example, systemic administration and administration in situ. Well-known viral delivery techniques include the use of adenovirus, retrovirus, lentivirus, foamy virus, herpes simplex virus, and adeno-associated virus viral constructs.

Preferred viral constructs are based on non-cytopathic eukaryotic viruses in which non-essential genes have been replaced with the gene of interest. Preferred viruses for certain embodiments of the invention are the adenoviruses and adeno-associated (AAV) viruses, which are single-stranded DNA viruses that have already been approved for human use in gene therapy.

a. Adenovirus Viral Constructs

One illustrative method for in vivo delivery of one or more nucleic acid sequences involves the use of an adenovirus expression viral construct. "Adenovirus expression viral construct" is meant to include those constructs containing adenovirus sequences sufficient to (a) support packaging of the construct and (b) to express the gene encoding the hp70S6K (CA) protein that has been cloned therein.

The viral construct comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus & Horwitz, 1992). Generation and propagation of the current adenovirus viral constructs, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus viral constructs, with the help of 293 cells, carry foreign DNA in either the E1, the D3, or both regions (Graham & Prevec, 1991).

Adenovirus viral constructs have been used in eukaryotic gene expression (Levrero et al., 1991; Gomez-Foix et al., 1992) and vaccine development (Grunhaus & Horwitz, 1992; Graham & Prevec, 1992). Recently, animal studies suggested that recombinant adenovirus could be used for gene therapy (Stratford-Perricaudet & Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993).

b. Adeno-Associated Viral Constructs (AAV)

By an "AAV construct" is meant a construct derived from an adeno-associated virus serotype of which there are twelve. The Examples herein describe how to make the AAV viral constructs that were used in the described experiments. All of the constructs used in the Examples were AAV1 serotype, however, while this represents a preferred embodiment, other useful serotypes can be determined by routine experimentation to identify the optimum construct depending on the targeted cells. This section provides a background on AAV constructs. Any methods known in the art can also be used to produce AAV constructs.

AAV is a good choice of delivery vehicles due to its safety, i.e., genetically engineered (recombinant) does not integrate into the host genome. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

Twelve different AAV serotypes (AAV1 to 12) are known, each with different tissue tropisms (Wu, Z Mol Ther 2006; 14:316-27). Five serotypes have been isolated, of which AAV2 is the best characterized. AAV has a single-stranded linear DNA that is encapsulated into capsid proteins VP1, VP2 and VP3 to form an icosahedral virion of 20 to 24 nm in diameter (Muzyczka & McLaughlin, 1988). Recombinant AAV is derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). AAV have advantages such as heat and lipid solvent stability, high transduction frequencies in cells of diverse lineages, and lack of superinfection inhibition thus allowing multiple series of transductions. In some embodiments of the invention, neurons (such as dopaminergic cells in the SN) are transduced with a gene delivery vehicle such as an AAV viral construct carrying the hp70S6K(CA) gene multiple times.

The adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Typically, viral constructs carrying transgenes are assembled from polynucleotides encoding the transgene, suitable regulatory elements and elements necessary for production of viral proteins which mediate cell transduction via integration of transferred gene into the genomic DNA of host cells.

Adeno-associated viruses are small, single-stranded DNA viruses which require helper virus to facilitate efficient replication (K. I. Berns, Parvoviridae: the viruses and their replication, p. 1007-1041, in F. N. Fields et al., Fundamental Virology, 3rd ed., vol. 2, (Lippencott-Raven Publishers, Philadelphia, Pa.) (1995)). The 4.7 kb genome of AAV is characterized by two inverted terminal repeats (ITR) and two open reading frames which encode the Rep proteins and Cap proteins, respectively. The Rep reading frame encodes four proteins of molecular weight 78 kD, 68 kD, 52 kD and 40 kD. These proteins function mainly in regulating AAV replication and rescue and integration of the AAV into a host cell's chromosomes. The Cap reading frame encodes three structural proteins of molecular weight 85 kD (VP 1), 72 kD (VP2) and 61 kD (VP3) (Berns, cited above) which form the virion capsid. More than 80% of total proteins in AAV virion comprise VP3.

Gene delivery vehicles, preferably AAV constructs, useful in the practice of the present invention can be constructed utilizing methodologies well known in the art of molecular biology. A constitutively active form of p70S6K(CA) was designed for inclusion in AAV constructs to transduce targeted neurons (for example dopaminergic neurons in the SN) by AAV-mediated gene transfer. The Gene Bank accession number for wild type p70S6K is NM3161. Wild type p70S6K protein becomes constitutively active by elimination of an autoinhibitory domain at the C-terminus and by mutation of a threonine residue at position 389 to glutamate, see SEQ ID NO. 1 for the nucleic acid sequence of the gene (hp70S6K (CA) used in the construct. The amino acid sequence of the constitutively active protein (hp70S6K (CA) is set forth in SEQ ID NO. 2. In an embodiment, adeno-associated viral (AAV) constructs are employed, with a preferred embodiment being AAV1 constructs that target degenerating neurons in the CNS. In another embodiment AAV2 constructs are used to target neurons. Certain other embodiments include without limitation, AAV-3, AAV-4, AAV-5, AAV-6, AAV-9, AAV-10, and AAV-11 constructs for use in transfecting/transducing neurons. Particularly preferred are viral constructs derived from AAV serotypes having tropism for and high transduction efficiencies in neurons of the mammalian CNS. A review and comparison of transduction efficiencies of different serotypes is provided din Davidson et al., 2000. In one embodiment, AAV2 based viral constructs are used as they have been shown to direct long-term expression of transgenes in CNS, preferably transducing neurons. In other embodiments, viral constructs derived from AAV1, AAV4 and AAV5 serotypes are used because they also transduce cells of the CNS (Davidson et al., supra).

AAV viral constructs can have one or more of the AAV wild-type genes deleted in whole or part, preferably the rep and/or cap genes, but retain functional flanking inverted terminal repeat [ITR] sequences. Functional ITR sequences are used for the rescue, replication and packaging of the AAV virion. Thus, an AAV viral construct is defined herein to include at least those sequences required for replication and packaging (e.g., functional ITRs) of the virus. The ITRs need not be the wild-type nucleotide sequences, and may be altered, e.g., by the insertion, deletion or substitution of nucleotides, as long as the sequences provide for functional rescue, replication and packaging. AAV expression viral constructs are constructed using known techniques to at least provide as operatively linked components in the direction of transcription, control elements including a transcriptional initiation region, the DNA of interest (i.e., the hp70S6K (CA) gene) and a transcriptional termination region. See, e.g., U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994. The AAV-hp70S6K(CA) gene construct described herein is a preferred embodiment.

The control elements are selected to be functional in a mammalian cell. The resulting construct which contains the operatively linked components is bounded (5' and 3') with functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, e.g., Kotin, 1994; Berns, K I "Parvoviridae and their Replication" in Fundamental Virology, 2nd Edition, (B. N. Fields and D. M. Knipe, eds.) for the AAV-2 sequence. The AAV ITR may be derived from any of several AAV serotypes. In embodiments of the present invention the AAV1 serotype is used. 5' and 3' ITRs which flank a selected nucleotide sequence in an AAV viral construct need not necessarily be identical or derived from the same AAV serotype or isolate, so long as they function as intended, i.e., to allow for excision and rescue of the sequence of interest from a host cell genome or viral construct, and to allow integration of the heterologous sequence into the recipient cell genome when AAV Rep gene products are present in the cell.

The AAV viral construct which harbors the DNA molecule of interest bounded by AAV ITRs, can be constructed by directly inserting the selected hp70S6KCA gene sequence(s) into an AAV genome from which the major AAV open reading frames ("ORFs") have been excised. Examples of constitutive promoters which may be included in the AAV of this invention include, without limitation, the exemplified CMV immediate early enhancer/chicken β-actin (CBA) promoter. In certain embodiments, the gene delivery vehicle is an AAV expression viral construct that comprises a chicken β-actin (CBA) promoter, an hp70S6K(CA) gene located downstream of the chicken β-actin promoter, a 3' woodchuck post-transcriptional regulatory element (WPRE (pBL)) located downstream of the hp70S6K(CA) gene, and a polyadenylation sequence (BGHpolyA) inserted before the 3' ITR sequence. In certain other embodiments, short peptide sequences, or zip codes, may be included in the gene delivery vehicle, such as the cAPP neuron targeting sequence.

In certain embodiments not only is the serotype selected to optimize delivery to neurons, but the construct also comprises a zip code for targeting the encoded protein to neurons. One of the best characterized mechanisms for local axonal mRNA translation is that of "zip code" binding protein (ZBP1) interaction with a 54 nt sequence in the 3' UTR of β-actin mRNA (11). In axons, ZBP1 and β-actin mRNA are co-localized and transported in axon granules (12). Initiation of translation of β-actin mRNA is regulated by Src phosphorylation of ZBP1 (13). A similar 91nt zip code exists in the 3' UTR of tau mRNA (14-15). In addition to these mRNA "zip codes," short peptide sequence "zip codes" have been identified in proteins. Sapute-Krishnan and colleagues (16) identified APP-C, which represents the final 15 amino acids of the 47-aa C terminus of amyloid precursor protein, which extends into the cytoplasm. This peptide, conjugated to polystyrene beads, was sufficient to mediate anterograde transport. This sequence (SEQ ID NO. 3: GYENPTYKFFEQMQN) was successfully used by Babetto et al. to target NMNAT (a mediator of axon protection) to axons in vivo in mice (17). Zuber and colleagues identified a peptide sequence in the N-terminus of GAP43, containing two cysteines, that serves as a palmitoylation signal and mediates targeting to growth cones (18). This sequence was again used successfully by Babetto et al. to target NMNAT to axons in vivo, and it was also used by Matsuda and colleagues to target GFP to the terminal arborizations of nigro-striatal dopaminergic axons. (19). Constructs in which the sequence for red fluorescent protein Tomato were modified to incorporate either a 3' UTR "zip code" or a short peptide sequence "zip code." Any of these zip codes and other zip codes for neuronal proteins can be used in the gene delivery vehicles of the present invention. In preferred embodiments the zip code is cAPP.

For eukaryotic cells, expression control sequences typically include a promoter, an enhancer such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA sequence may be used.

The regulatory sequences useful in the constructs of the present invention may also contain an intron, desirably located between the promoter/enhancer sequence and the gene. One possible intron sequence is also derived from SV-40, and is referred to as the SV-40 T intron sequence. Another suitable sequence includes the (WPRE) or woodchuck hepatitis virus post-transcriptional element. (See, e.g., L. Wang and I. Verma, 1999 Proc. Natl. Acad. Sci., USA, 96:3906-3910.)

Alternatively, AAV ITRs can be excised from the viral genome or from an AAV viral construct containing the same and fused 5' and 3' of a selected nucleic acid construct that is present in another viral construct using standard ligation techniques. AAV viral constructs which contain ITRs have been described in, e.g., U.S. Pat. No. 5,139,941. In particular, several AAV viral constructs are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge, 1981; Nambair et al., 1984; Jay et al., 1984. In order to produce rAAV virions, an AAV expression viral construct is introduced into a suitable host cell using known techniques, such as by transfection. A number of transfection techniques are generally known in the art. See, e.g., Graham et al., 1973; Sambrook et al. (1989) Molecular Cloning, a laboratory manual, Cold Spring Harbor Laboratories, New York, Davis et al. (1986) Basic Methods in Molecular Biology, Elsevier, and Chu et al., 1981. Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Feigner et al., 1987), and nucleic acid delivery using high-velocity microprojectiles (Klein et al., 1987).

Selection of these and other common viral construct and regulatory elements are conventional and many such sequences are available. See, e.g., Sambrook et al., and references cited therein at, e.g., pages 3.18-3.26 and 16.17-16.27 and Ausubel et al., Current Protocols in Molecular Biology, John Wiley & Sons, New York, 1989). Of course, not all viral constructs and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct.

Methods of delivery of viral constructs to neurons include generally any method suitable for delivery viral constructs to the targeted neurons such that at least a portion of cells of targeted neurons are transduced.

To deliver the viral construct specifically to a particular region and to a particular population of cells of the CNS, the viral construct may be administered by stereotaxic microinjection. For example, patients have the stereotactic frame base fixed in place (screwed into the skull). The brain with stereotactic frame base (MRI compatible with fiducial markings) is imaged using high resolution MRI. The MRI images are then transferred to a computer which runs stereotactic software. A series of coronal, sagittal and axial images are used to determine the target (site of AAV viral construct injection) and trajectory. The software directly translates the trajectory into 3 dimensional coordinates appropriate for the stereotactic frame. Burr holes are drilled above the entry site and the stereotactic apparatus positioned with the needle implanted at the given depth. The AAV viral construct is then injected at the target sites. Since the AAV viral construct integrates into the target cells, rather than producing viral particles, the subsequent spread of the viral construct is minor, and mainly a function of passive diffusion from the site of injection and of course the desired transsynaptic transport, prior to integration. The degree of diffusion may be controlled by adjusting the ratio of viral construct to fluid carrier.

The target neurons of the viral constructs of the present invention are cells of the central nervous system of a subject afflicted a neurodegenerative disease such as Parkinson's disease, Alzheimer's disease, or Huntington's disease, preferably neural cells. Preferably the subject is a human being. In embodiments for Alzheimer's disease the neurons in the cerebral cortex, cingulate gyrus, and brainstem nuclei are targeted. In Huntington's disease neurons in the basal ganglia are targeted.

However the invention encompasses delivering the viral construct to biological models of the disease. In that case, the biological model may be any mammal at any stage of development at the time of delivery, e.g., embryonic, fetal, infantile, juvenile or adult, preferably it is an adult. Furthermore, the target CNS cells may be essentially from any source, especially nonhuman primates and mammals of the orders Rodenta (mice, rats, rabbit, hamsters), Carnivora (cats, dogs), and Arteriodactyla (cows, pigs, sheep, goats, horses) as well as any other non-human system (e.g. zebrafish model system).

c. Retrovirus Viral Constructs

In certain embodiments, the viral construct may be a retroviral construct. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression viral constructs have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991.

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants.

The retroviral genome contains three genes, gag, pol, and env, that code for capsid proteins, polymerase enzyme, and envelope components, respectively. A sequence found upstream from the gag gene contains a signal for packaging of the genome into virions. Retroviral constructs are gene transfer plasmids wherein the heterologous nucleic acid resides between two retroviral LTRs. Retroviral constructs typically contain appropriate packaging signals that enable the retroviral construct, or RNA transcribed using the retroviral construct as a template, to be packaged into a viral virion in an appropriate packaging cell line (see, e.g., U.S. Pat. No. 4,650, 764). These two long terminal repeat (LTR) sequences are present at the 5' and 3' ends of the viral genome. These contain strong promoter and enhancer sequences and are also required for integration in the host cell genome (Coffin, 1990). In order to construct a retroviral construct, a nucleic acid encoding one or more oligonucleotide or polynucleotide sequences of interest is inserted into the viral genome in the place of certain viral sequences to produce a virus that is replication-defective. Also included are episomal or non-integrating forms of retroviral constructs based on lentiviruses (e.g., a type of retrovirus).

Suitable retroviral constructs for use herein are described, for example, in U.S. Pat. Nos. 5,399,346 and 5,252,479; and in WIPO publications WO 92/07573, WO 90/06997, WO 89/05345, WO 92/05266 and WO 92/14829, which provide a description of methods for efficiently introducing nucleic acids into human cells using such retroviral constructs. Other retroviral constructs include, for example, mouse mammary tumor virus viral constructs (e.g., Shackleford et al., Proc. Natl. Acad. Sci. U.S.A. 85:9655-9659 (1998)), lentiviruses, and the like. An exemplary viral construct is plentilox-IRES-GFP.

d. Transfection of Viral Constructs

Viral constructs can also be used for transfection of a mammalian cell such as a neuron and introducing a polynucleotide into its genome. In an indirect method, viral constructs, carrying genetic information, are used to infect target cells removed from the body, and these cells are then re-implanted. Direct in vivo gene transfer into postnatal animals has been reported for formulations of DNA encapsulated in liposomes and DNA encapsulated in proteoliposomes containing viral envelope receptor proteins (Nicolau et al., Proc. Natl. Acad. Sci USA 80:1068-1072 (1983); Kaneda et al., Science 243:375-378 (1989); Mannino et al., Biotechniques 6:682-690 (1988). Viral constructs can be injected or transduced into host neurons in vitro (Nakajima, A., et al., J. Clin. Invest., vol. 17(21), p. 1293-1310 (2001) and Tuohy, V. K., et al., J. Neuroimmunol., vol. 17(2), p. 226-32 (2000)), fibroblasts (Rabinovich, G. A., et al., J. Exp. Med., vol. 19, p. 385-98 (1999)), dendritic cells (DCs) (Kim, S. H., et al., J. Immunol., vol. 166(21), p. 3499-3550 (2001) and Morita, Y., et al., J. Clin. Invest., vol. 17(21), p. 1275-84 (2001)) and stem cells (ATCC or autologous).

e. Other Viral Constructs as Expression Constructs

Other viral constructs may be employed as expression constructs in the present invention for the delivery of oligonucleotide or polynucleotide sequences to a host cell. Viral constructs derived from viruses such as vaccinia virus (Ridgeway, 1988; Coupar et al., 1988), polioviruses and herpes viruses may be employed. They offer several attractive features for various mammalian cells (Friedmann, 1989; Ridgeway, 1988; Coupar et al., 1988; Horwich et al., 1990). Also included are hepatitis B viruses (Horwich et al., 1990; and Chang et al., 1991).

Non-Viral Constructs a. Plasmid Viral Constructs

Nonviral constructs include plasmid viral constructs. Plasmid viral constructs have been extensively described in the art and are well known to those of skill in the art. See e.g. Sambrook et al., 1989. In the last few years, plasmid viral constructs have been used as DNA vaccines for delivering antigen-encoding genes to cells in vivo. They are particularly advantageous for this because they do not have the same safety concerns as with many of the viral constructs. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of routes. For example, the DNA plasmid can be injected by intramuscular, intradermal, subcutaneous, or other routes. locally to the degenerating CNS neuron. The plasmids may be given in an aqueous solution, dried onto gold particles or in association with another DNA delivery system including but not limited to liposomes, dendrimers, cochleate and microencapsulation.

In order to effect expression of gene sequences, the expression construct must be delivered into a cell. This delivery may be accomplished in vitro, as in laboratory procedures for transforming cells lines, or preferably, in vivo or ex vivo, as in the treatment of certain disease states. In certain embodiments of the invention, an expression construct may simply consist of naked recombinant DNA or plasmids. Transfer of the construct may be performed by any of the methods mentioned above which physically or chemically permeabilize the cell membrane (see Dubensky et al., (1984); and Benvenisty & Reshef (1986)). Another embodiment of the invention for transferring a naked DNA expression construct into cells may involve particle bombardment. (See Klein et al., 1987; Yang et al., 1990; and Zelenin et al., 1991.) The microprojectiles used have consisted of biologically inert substances such as tungsten or gold beads.

Biodegradable microspheres (e.g., polylactate polyglycolate) may be employed as carriers for the gene delivery vehicles comprising the hp70S6K(CA) gene. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252.

Biodegradable polymeric nanoparticles facilitate nonviral gene transfer to human embryonic stem cells (hESCs). Small (approximately 200 nm), positively charged (approximately 10 mV) particles are formed by the self-assembly of cationic, hydrolytically degradable poly(beta-amino esters) and plasmid DNA.

Biologically Active Fragments or Variants a. Gene Variants

There may be multiple variants of any given gene in the human population (genes), leading to polymorphism. For example, one of ordinary skill in the art would acknowledge that nucleotide diversity may be based on single mutations called single nucleotide polymorphisms (SNPs). SNPs are changes in a single nucleotide when alleles are compared. Genes encoding the constitutively active mutant—hp70SK (CA)—protein used in the present invention may include well-known nucleotide modifications in the gene that can occur without removing the biological activity of the protein.

b. Protein Variants

As defined above, the "hp70SK(CA)" protein (herein also referred to interchangeably as polypeptide) includes all biologically active forms, fragments and variants that retain the biological activity of stimulating axon regeneration in a degenerating neuron of the CNS. For example dopaminergic neurons in the SN that are involved in PD, and degenerated neurons in other neurodegenerative diseases such as AD or HD, and brain and spinal cord injuries as a result of axon death. Biologically active fragments and biologically forms of the protein are used interchangeably and include functional variants of the protein for use in the present embodiments. Non-human forms of the hp70SK(CA) protein are also included in certain embodiments.

The hp70SK(CA) polypeptide may have variations in amino acid sequence, molecular weight, isoelectric point, the presence or absence of sugar chains, or form, depending on the cell or host used to produce it or the purification method utilized. Such functional equivalents include those wherein one or more amino acids are by one or more substitutions, deletions, insertions, inversions, fusions, and truncations or a combination of any of these. So long as the activity the protein is maintained, the number of amino acid mutations is not particularly limited. However, it is generally preferred to alter 5% or less of the amino acid sequence. Accordingly, in a preferred embodiment, the number of amino acids to be mutated in such a mutant is generally 30 amino acids or less, preferably 20 amino acids or less, more preferably 10 amino acids or less, more preferably 6 amino acids or less, and even more preferably 3 amino acids or less.

Variants of the hp70SK(CA) protein or biologically active fragments thereof, include forms that are substantially homologous but derived from another organism, i.e., an ortholog; substantially homologous proteins or peptides that are produced by chemical synthesis or by recombinant methods. As used herein, two proteins (or a region of the proteins or peptides) are substantially homologous when the amino acid sequences are at least about 70-75%, typically at least about 80-85%, and most typically at least about 90-95%, 97%, 98% or 99% or more homologous. Variants include conservative amino acid Substitutions: Aromatic Phenylalanine Tryptophan Tyrosine Hydrophobic Leucine Isoleucine Valine Polar Glutamine Asparagine Basic Arginine Lysine Histidine Acidic Aspartic Acid Glutamic Acid Small Alanine Serine Threonine Methionine Glycine.

Substantial homology can be to the entire amino acid sequence or to fragments of these sequences, which can be derived from the amino acid sequence of hp70SK(CA). However, the invention also encompasses fragments of the hp70SK(CA). Accordingly, a fragment can comprise any length that retains one or more of the desired biological activities of the protein, for example the ability to regenerate axons. Fragments can be discrete (not fused to other amino acids or polypeptides) or can be within a larger polypeptide, in which case the viral construct would have the nucleic acid sequence required for the full fused protein.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described below.

Biologically active/functional variants typically contain only conservative variation or variation in non-critical residues or in non-critical regions. Functional variants can also contain substitution of similar amino acids, which results in no change or an insignificant change in function. Certain substitutions may positively or negatively affect the enumerated biological activity to some degree. Variants can be naturally-occurring or can be made by recombinant means of chemical synthesis to provide useful and novel characteristics of the desired protein.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a proprotein sequence.

An amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Conservative substitution tables providing functionally similar amino acids are well known in the art. For example, the following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins 1984).

Such conservatively modified polypeptides are included in the present protein. However, the present invention is not restricted to these, and the hp70S6K(CA) protein includes non-conservative modifications, so long as at least one relevant biological activity of the protein is retained. Furthermore, the modified proteins do not exclude polymorphic variants, interspecies homologues, and those encoded by alleles of these proteins.

The hp70S6K(CA) protein also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Pharmaceutical Compositions or Formulations and Administration

The viral constructs used herein may be formulated in any suitable vehicle for delivery. For instance, in certain embodiments, the gene delivery vehicles or constructs e.g., AAV-hp70S6K(CA) or AAV-cAPP-hp70S6K(CA), can be placed into a pharmaceutically acceptable suspension, solution or emulsion. Generally, such carriers should be nontoxic to recipients at the dosages and concentrations employed.

Ordinarily, the preparation of such compositions entails combining the construct with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes.

The pharmaceutical compositions of the present invention may be prepared for administration by injection to the target area of the CNS, e.g., the SN for the treatment of PD. Further within other embodiments the constructs provided herein may be admixed with other carriers (e.g., polymers), and implanted on or contained within devices which are designed to release such constructs. Within further embodiments, the compounds may be delivered under radioscopic or other visual guidance to a desired site.

Sterile injectable solutions can be prepared by incorporating the gene delivery vehicle such as AAV-hp70S6K(CA) in the required amount in an appropriate solvent with one or a combination of the ingredients known in the art, as required, followed by filter sterilization.

The preferred doses and regimen may be determined by a physician, and depend on the age, sex, weight, of the subject, and the stage of the disease. Preferably, a single injection of AAV-hp70S6K(CA) or AAV-cAPP-hp70S6K(CA) would be given, however multiple injections may be needed.

Pharmaceutical compositions of the present invention may be placed within containers, or kits, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

5. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Materials and Methods

Chemical Reagents

Chemical reagents were obtained from SIGMA. 6OHDA was obtained from Regis Laboratories in Illinois, but may be obtained from other companies.

Mice and Animal Care

Adult (8 week) male C57Bl/6 mice weighing ~25 g were obtained from Charles River Laboratories (Wilmington, Mass.). TH-GFP transgenic mice, which express green fluorescent protein driven by the tyrosine hydroxylase (TH) promoter (11) were generously made available by Drs. K. Kobayashi and H. Okano and maintained on a C57B1/6 background.

Institutional Review of Animal Protocols

All injection procedures, described below, were approved by the Columbia University Animal Care and Use Committee.

Production of Adeno-Associated Virus (AAV) Viral Construct Hp70S6K(CA)

All viral constructs used for these studies were AAV1 serotype. The cDNA clone for wild type human p70S6K was obtained from OriGene Technologies (Catalogue No.; Accession No. NM_003161). A constitutively active mutant, in which a C-terminus autoinhibitory domain (aa399-502) is deleted and a threonine at position 389 is changed to a phospho-mimetic glutamate (hp70S6K(DELC/T389E) also referred to herein by the shorthand form as hp70S6K(CA)), has been previously characterized in in vitro studies (Zhang et al., 2006). This mutation was introduced by PCR-based site directed mutagenesis (Phusion Kit, New England Biolabs), and a 3'-end FLAG-encoding sequence was incorporated.

This modified constitutively active form of hp70S6K was then cloned into an AAV packaging construct that utilizes the chicken β-actin (CBA) promoter, and contains a 3' WPRE (pBL) (Kim et al., 2011) and a bovine growth hormone polyadenylation sequence (BGHpolyA). One of ordinary skill in the art would recognize that the viral construct may further include, but is not limited to, an origin of replication, regulatory sequences, selectable markers, tags, and unique restriction sites. All nucleotide sequences in the AAV packaging constructs were confirmed before AAV production. AAVs were produced by the University of North Carolina Viral construct Core. The genomic titer of AAV hp70S6K(DELC/T389E) was $1\times10^{12}$ viral genomes/mL, and that of AAV hSGK1(S422D) was also $4\times10^{12}$ viral genomes/mL.

Intranigral AAV injection

Mice were anesthetized with ketamine/xylazine solution and placed in a stereotaxic frame (Kopf Instruments) with a mouse adapter. The tip of 5.0 µL syringe needle (26S) was inserted to stereotaxic coordinates AP: −0.35 cm; ML: +0.11 cm; DV: −0.37 cm, relative to bregma. Viral construct suspension in a volume of 2.0 µL was injected at 0.1 µL/min over 20 minutes.

6-OHDA Lesion

Mice were first pretreated with desipramine to block 6-OHDA uptake by noradrenergic terminals, thereby limiting the lesion to striatal dopaminergic terminals. They were then anesthetized with ketamine/xylazine solution, and placed in a stereotaxic frame. A solution of 6-OHDA (5.0 µg/µl in 0.9% NaCl/0.02% ascorbate) was injected by microliter syringe at a rate of 0.5 µl/minute by pump for a total dose of 15.0 µg/3 µl. The injection was performed into the left striatum at coordinates AP: +0.09 cm; ML: +0.22 cm; DV: −0.25 cm relative to bregma. After a wait of 2 minutes, the needle was withdrawn slowly. 6-OHDA in the striatum causes retrograde degeneration of dopaminergic axons projecting to the striatum from the substantia nigra.

Immunohistochemistry

For TH immunostaining, mice were perfused through a cannula placed in the left ventricle with 0.9% NaCl followed by 4.0% paraformaldehyde in 0.1 mol/l phosphate buffer, pH 7.1. The brain was carefully removed and blocked into midbrain and forebrain regions. The region containing the midbrain was postfixed for 1 week, cryoprotected in 20% sucrose overnight, and then rapidly frozen by immersion in isopentane on dry ice. A complete set of serial sections was then cut through the SN at 30 µm. Beginning with a random section between and 4, every fourth section was processed, in keeping with the fractionator method of sampling (see below). Sections were processed free-floating. The primary antibody was rabbit anti-TH (Calbiochem, La Jolla, Calif.) at 1:750. Sections were then treated with biotinylated protein A and avidin-biotinylated horseradish peroxidase complexes (ABC; Viral construct Labs, Burlingame, Calif.). After immunoperoxidase staining, sections were thionin counterstained. The forebrain region containing the striatum was postfixed for 48 hours, frozen without cryoprotection, and processed as described previously. (51). Immunostaining for DAT was performed with rat anti-DAT (Chemicon, Temecula, Calif.) at 1:1,000, and for neuron-specific nuclear protein (NeuN) with a mouse monoclonal antibody at 1:100 (Chemicon). Sections were incubated with biotinylated anti-rat or anti-mouse IgG (Viral construct Labs), respectively, followed by ABC (Viral construct Labs). For immunostaining of the FLAG epitope, sections were initially treated with Mouse-on-Mouse Blocking Reagent (Viral construct Labs) and processed free-floating with a mouse monoclonal anti-FLAG antibody (Sigma, St Louis, Mo.) at 1:1,000. Sections were incubated with biotinylated anti-mouse IgG (Viral construct Labs), followed by ABC (Viral construct Labs). For immunofluorescent staining, fluorescein conjugated avidin was used after secondary antibody. Phosphorylated-4E-BP1 immunostaining was performed on 30 µm sections with a rabbit anti-phospho-4E-BP1 (Thr37/46) antibody (Cell Signaling, Beverly, Mass.) at 1:200. Sections were treated with biotinylated protein A and avidin-biotinylated horseradish peroxidase complexes (ABC; Viral construct Labs). After immunoperoxidase staining, sections were thionin counterstained.

Quantitative Determination of SN Dopamine Neuron Numbers and Striatal TH Immunoperoxidase Staining Density SN dopamine neuron numbers were determined by stereologic analysis under blinded conditions using StereoInvestigator software (MicroBrightField, Williston, Vt.). The optical density of striatal TH immunostaining was determined with an Imaging Research (St. Catherines, Ontario) Analytical Imaging Station.

Quantification of GFP-Positive Axons and Tomato-Tau-Positive Axons in the Medial Forebrain Bundle (MFB)

Quantification of axons was performed on TH-GFP transgenic mice, which express green fluorescent protein driven by the TH promoter (11). Mice were perfused intracardially with 0.9% of NaCl followed by 4.0% paraformaldehyde in 0.1M phosphate buffer (pH 7.1), and then post fixation for 48 hours. The brains were sectioned horizontally on a Vibratome at 50 µm. A section containing the posterior third ventricular recess and the A13 dopamine cell group was selected for analysis as described (20). Confocal microscopy (Leica TCS SP5 AOBS MP System) was used to acquire images through the entire medial-to-lateral extent of the MFB. Proceeding from a point midway between the anterior A13 cells and the posterior third ventricle recess, images were acquired with a 20× objective with a zoom factor of 8 applied. Seven contiguous fields (97 µm×97 µm) were scanned. Each field was scanned in the Z-axis with twenty 0.1 µm thickness optical planes from dorsal to ventral, for a total vertical distance of 2.0 µm in the center of the section. These twenty optical planes were then merged to obtain a single maximal projection of the sampled volume. In order to count the number of axons passing in the rostro-caudal dimension through each sample volume, two horizontal sampling lines were drawn on the image at a separation distance of 10 µm in the center of the maximal projection. Every intact axon crossing both lines was counted as positive. An identical approach was used to count tomato-positive axons. In addition, tortuous tomato-positive axons in the MFB were identified by epifluorescence.

Statistical Analysis

Differences between two groups were analyzed by the Student t-test. Multiple comparisons among groups were performed by one-way ANOVA and Tukey's post hoc analysis. All statistical analyses were performed using SigmaStat software (Systat Software, San Leandro, Calif.).

Example 2

Mediators of Axon Growth in the Dopaminergic Nigro-Striatal Projection

Figure 2A:
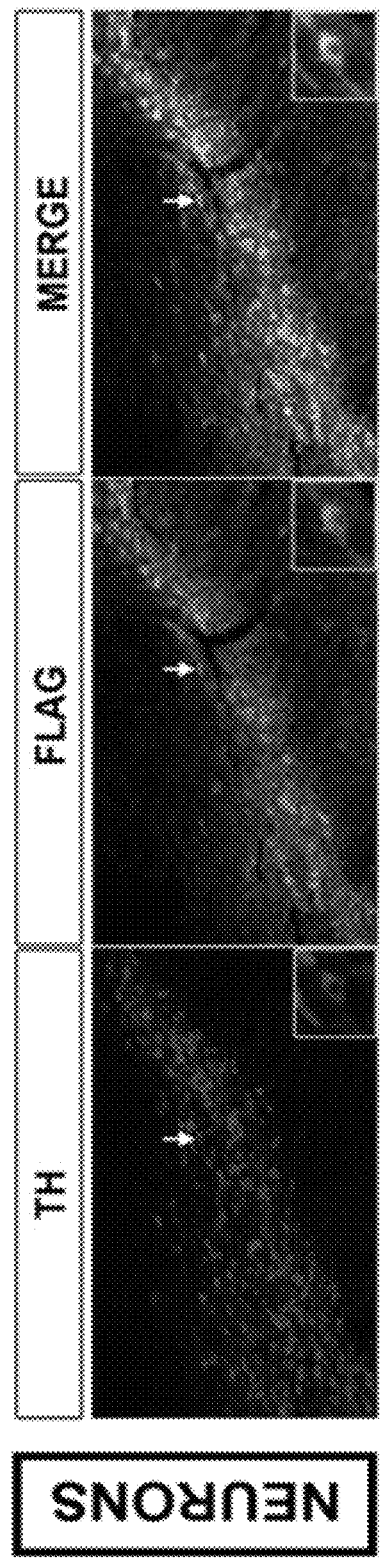
FIG. 2A-C represents expression patterns and function of AAV hp70S6K (CA).

At time=0, mice received a unilateral intra-striatal injection of 6-OHDA. At time=3 weeks, the mice received either AAV-p70S6K(WT) or AAV-p70S6K(delC/T389E) (also referred to herein as AAV-p70S6K (CA)) or control AAV-GFP. At Time=15 weeks (12 weeks post AAV) mice were sacrificed by perfusion fixation and immunostaining for TH on coronal SN and striatal sections were performed. Transduction of the substantia nigra pars compacta (SNpc) dopamine neurons with AAV-hp70S6K(CA) was demonstrated by immunoperoxidase staining for the FLAG epitope, and by double immunofluorescence labeling for FLAG and tyrosine hydroxylase (TH) (FIG. 2A).

Figure 2B:
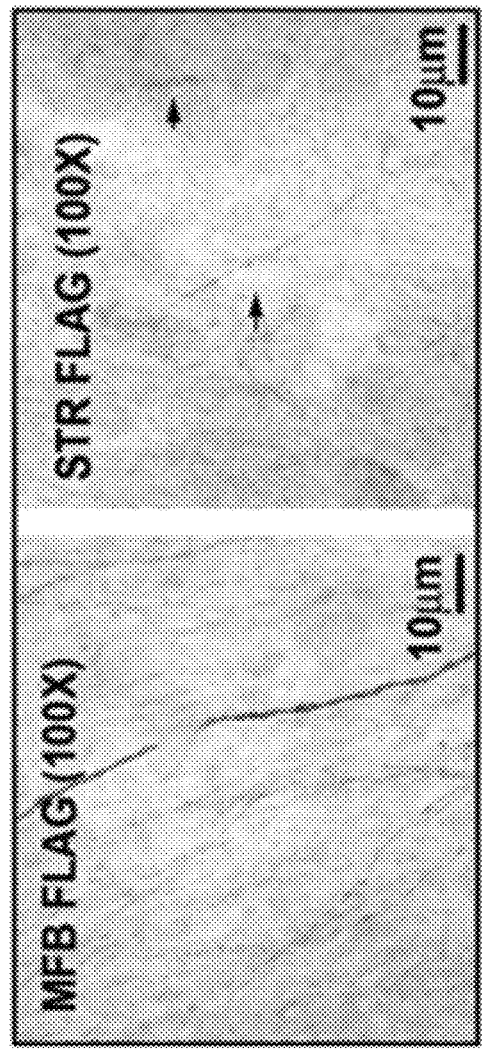
Figure 2C:
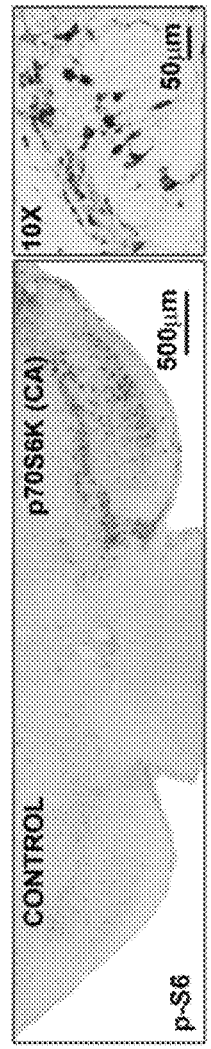

The number of remaining SN dopamine neurons were determined by sterologic counting. The density of TH immunoperoxidase staining in the lesioned striatum was determined, and expressed as a percent of the optical density of the contralateral, non-lesioned striatum, which serves as an internal control for each section. For these experiments, based on our previous experience with this model, an N=8 in each group provided sufficient power to detect an effect. The upper panel (FIG. 2A) indicates immunofluorescence double-labeling for TH (red) and FLAG (green) demonstrates that transgene expression is identifiable within dopamine neurons of the SNpc for each viral construct. Each viral construct was estimated to achieve efficiencies of transduction of dopamine neurons ranging from 80% in the caudal planes adjacent to the viral construct injection site to 60% in the rostral planes. FIG. 2B shows that hp70S6K(CA) protein is expressed by the axons.

hp70S6K(CA) induces a detectable increase in phosphorylation of ribosomal protein S6. This induced phosphorylation by hp70S6K(CA) in the SN was demonstrated by immunoperoxidase staining to occur exclusively within neurons of the SNpc (FIG. 2C).

Example 3

AAV-hp70S6K(CA) Effects in Normal Adult Mice

Figure 3A:
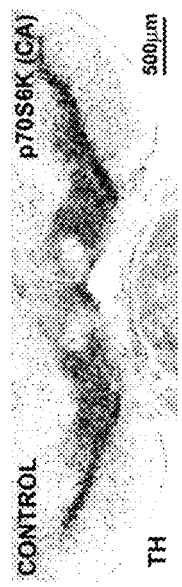
Figure 3C:
Figure 3D:
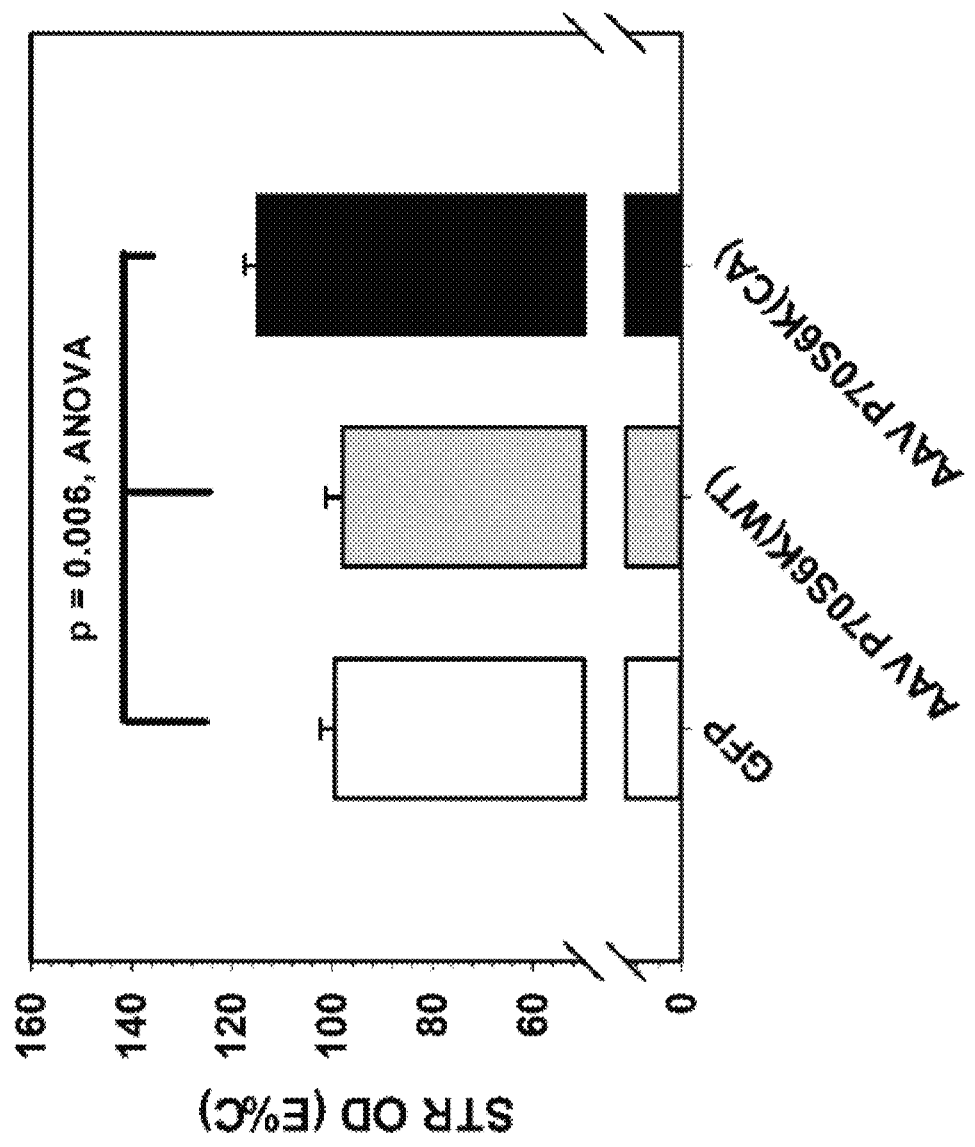

The effects of AAV-hp70S6K(CA) transduction of normal adult, non-lesioned mice are shown in FIG. 3A-D. An increased density of immunostaining for TH in the striatum was seen and it is most likely due to the induction of sprouting of dopaminergic nerve fibers in the striatum. In normal mice, AAV-hp70S6K(CA) did not induce the formation of new axons. Morphologic analysis of SN dopamine neurons at 5-6 weeks after intranigral injection of AAV-hp70S6K(CA) was conducted using tyrosine hydroxylase (TH) immunoperoxidase staining and thionin counterstaining. The experimental side injected with AAV-hp70S6K(CA) shows an increased density of staining that is associated with an increase in the mean area of the TH-positive neurons FIG. 3(A). A morphologic analysis of the striatum of these AAV-hp70S6K(CA) transduced animals at 5-6 weeks is shown in FIG. 3B. FIG. 3C is a morphologic analysis of the corpus striatum at 5-6 weeks after intranigral injection of AAV-hp70S6K(CA). A representative coronal section of TH immunoperoxidase staining reveals an increased density of staining on the experimental side injected with AAV-hp70S6K(CA). AAV-hp70S6K(CA) induced a 1.2-fold increase in optical density (OD) of TH peroxidase stain, expressed as percent of the contralateral, noninjected side, in comparison to AAV green fluorescent protein (GFP)-injected mice (P-0.005, one-way ANOVA and Tukey post-hoc analysis as shown; n=8 animals, each experimental group). FIG. 3D.

Example 4

Quantification of Dopaminergic Axons in the Median Forebrain Bundle

Figure 4A:
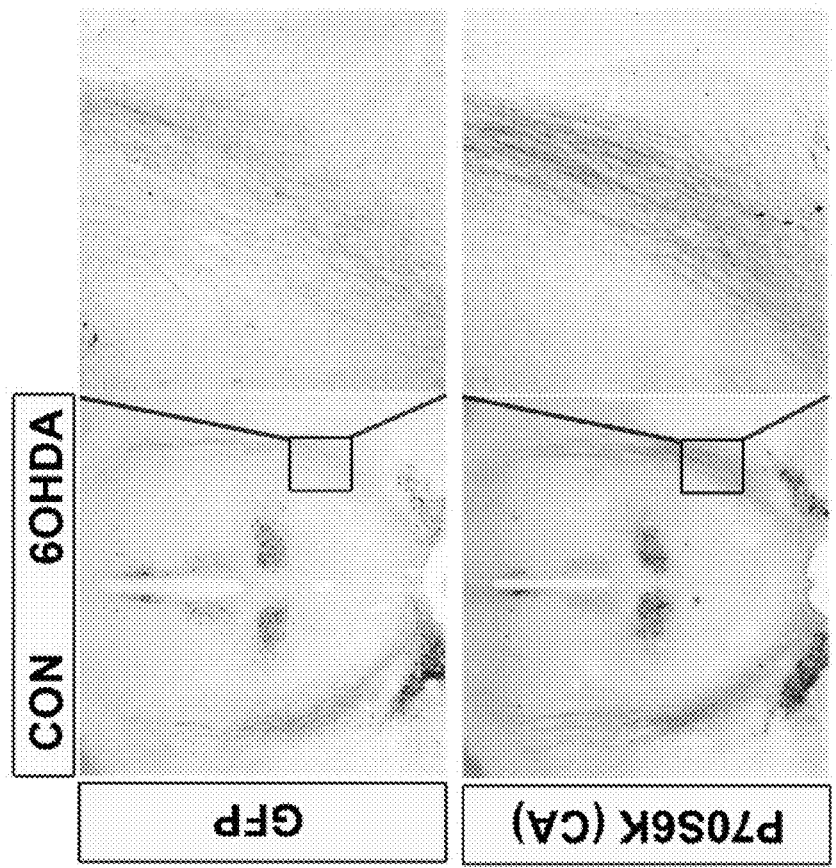

The effects of post intra-striatal 6-OHDA injection are shown in FIG. 4. Mice were subjected to 6-OHDA lesion, injected with AAV-hp70S6K(CA), and at time=12 weeks post-lesion, mice were sacrificed by perfusion fixation. The brains were sectioned horizontally, immunostained for TH, and quantitatively analyzed for the number of TH-positive axons in the MFB. In mice treated with AAV-hp70S6K(CA), there was a significant reinnervation of the MFB and striatum, as shown by peroxidase staining for TH as shown in (FIG. 4(A)). Representative horizontal sections stained for TH are shown at 15 weeks post-lesion. The red rectangles encompass the MFB on the lesioned side, and are shown at higher magnification in the panels at the right. The effect of hp70S6K (CA) is shown quantitatively as TH-positive axon counts in FIG. 4(B). These mice (N=9) had a mean of 69.4 axons on the lesioned side, whereas AAV-GFP (N=8) and AAV-hp70S6K injected mice (N=8) had only 41.9 and 49.8 axons, respectively, a highly significant different [$P<0.005$, ANOVA; Tukey post-hoc comparisons.]

Example 5

Quantification of GFP-Positive Axons and Tomato-Tau-Positive Axons in the MFB

The effects of post intra-striatal 6-OHDA injection performed in transgenic TH-GFP mice is shown in FIG. 5. These mice express GFP in the dopaminergic axons, making it possible to quantify them without relying on the expression of TH protein. While immunostaining for TH, or other protein markers of dopamine axons, provides a useful static picture of the extent of striatal and MFB axon restoration, it is not useful for monitoring dynamic aspects of dopaminergic axon growth, because TH is highly regulated, and in some contexts, there is no expression even in structurally intact axons.

Figure 5A:
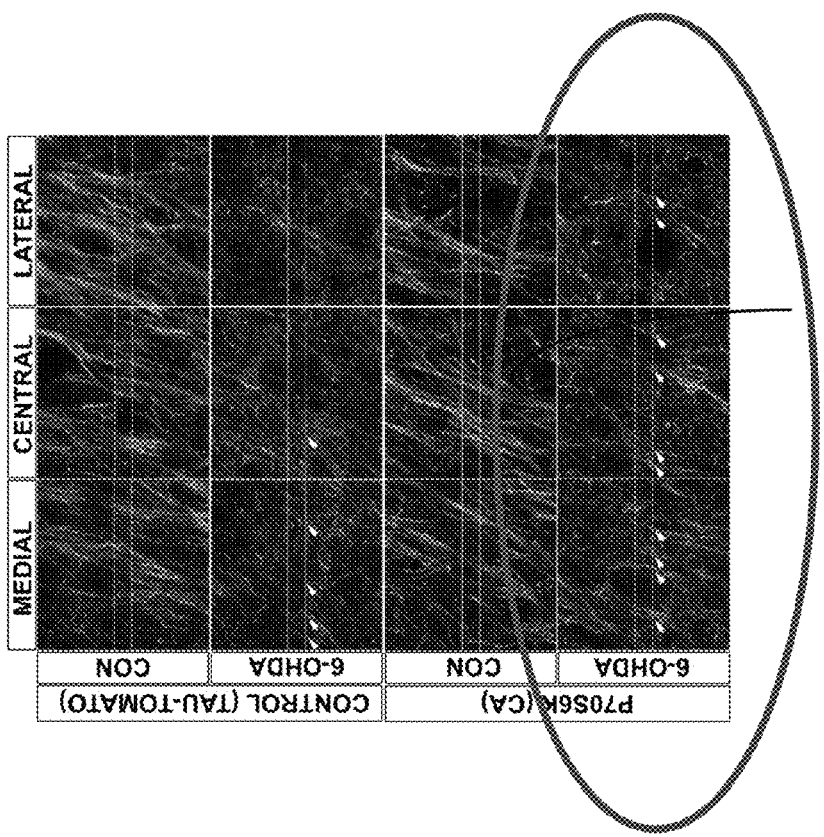
FIG. 5A-B show a reconstruction of the dopaminergic projection within the medial forebrain bundle (MFB) by axons from the SNpc. Each panel represents a single confocal maximal projection of a 20×0.1 µM Z stack acquired from the MFB of a TH-GFP mouse. For each representative set of panels acquired from a single mouse, three images are shown from the central and adjacent medial and lateral MFB on both the non-lesioned control (CON) and the GFP-positive axons on the 6OHDA-lesioned side. It can be seen that there are more axons in the MFB on the 6OHDA-lesioned side of mice treated with p70S6K (CA) in comparison to control mice, injected with AAV Tau-Tomato. This effect is shown quantitatively in the graph.
Figure 5B:
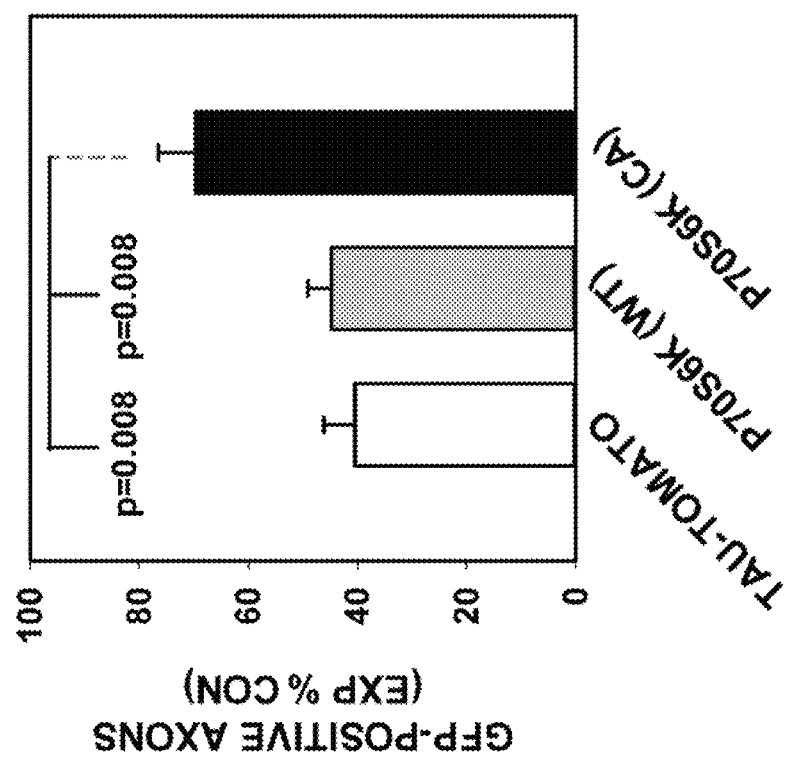

In order to monitor the growth of new axons from the SN through the MFB towards the striatum, two techniques were utilized. First, TH-GFP transgenic mice were used to monitor the presence of dopaminergic axons in the MFB without dependence on the TH expression phenotype (31). (FIG. 5). In FIG. 5(A), each panel represents a single confocal maximal projection of a 20×0.1 µl Z stack acquired from the MFB of a TH-GFP mouse. For each representative set of panels acquired from a single mouse, three images are shown from the central and adjacent medial and lateral MFB on both the non-lesioned control (CON) and the 6OHDA-lesioned side. FIG. 5(A). There are more axons in the MFB on the 6-OHDA-lesioned side of mice treated with p70S6K(CA) compared to control mice injected with AAV Tau-Tomato. This effect is shown quantitatively in the graph. Quantitative analysis, shown in the graph to the right (FIG. 5(B)), reveals that there is an increase in axon growth in mice receiving AAV-hp70S6K(CA.

Figure 6A:
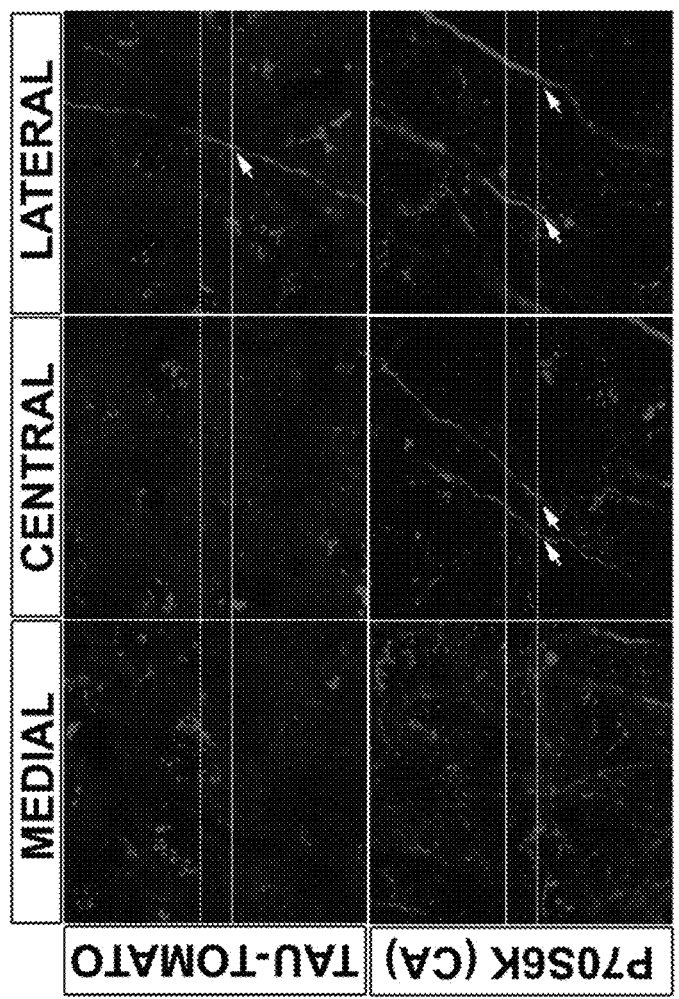
FIG. 6A-B are representative confocal Z-stacks from central and adjacent medial and lateral MFB on the lesioned side shown at 15 weeks post-lesion. They are reflective of the restoration of axons as revealed by a technique in which axons are visualized by expression of an axonal marker, Tomato-tau, a fluorescent fusion protein that traffics to axons. SN neurons are transduced with AAV Tom-Tau at time of simultaneous AAV hp70S6K (CA) transduction and then visualized and counted at 12 weeks post-transduction (FIG. 6A).
Figure 6B:
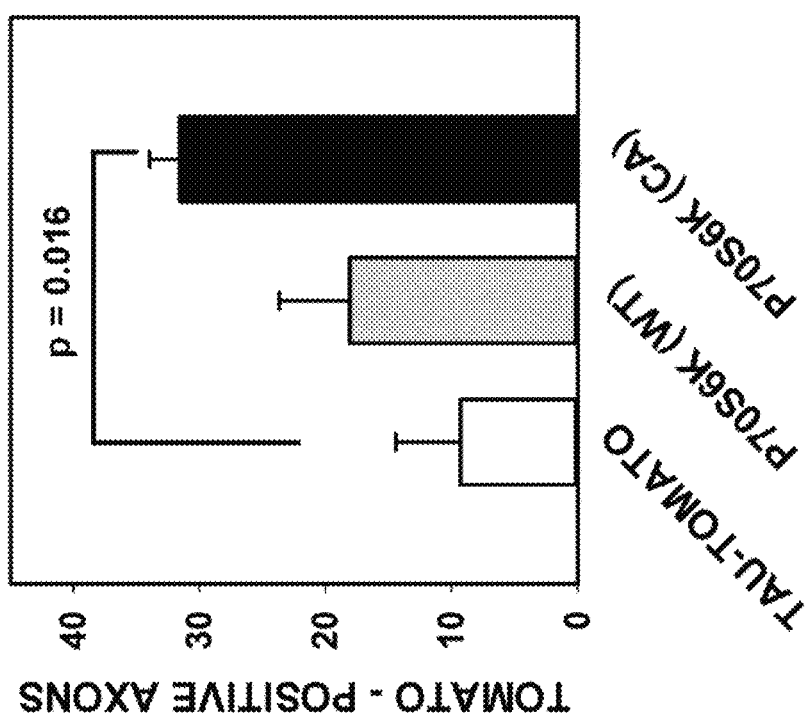

The restoration (regeneration/regrowth) of axons in lesioned mice was revealed by a technique in which axons are visualized by expression of the axonal marker, Tomato-tau. Tomato-tau is a fluorescent fusion protein that traffics to axons. (FIG. 6(A)). SN neurons were transduced with AAV-Tomato-tau simultaneously with AAV-hp70SK(CA) transduction, and then visualized and counted at 12 weeks post-transduction. Tomato-tau transduction also enables quantification of axons without relying on expression of TH protein. Quantitative analysis, shown in the graph to the right (FIG. 6(B)), revealed that there is an increase in axon regrowth in mice receiving AAV-hp70S6K(CA). Specifically, mice transduced with AAV-hp70S6K(CA) showed an increased number of tomato-tau-positive axons in the MFB. These mice had a mean of 30 axons on the lesioned side whereas mice injected with tomato-tau injected alone and P70S6K (WT) mice had only 10 and 15 axons, respectively, a highly significant different [P<0.016], ANOVA, Tukey post-hoc comparisons as shown in FIG. 6(B). Because expression of Tomato-tau is driven by the CBA promoter, the visualization of axons by this technique does not depend on activation of the TH promoter.

REFERENCES

1. Filbin M T. Recapitulate development to promote axonal regeneration: good or bad approach? Philos Trans R Soc L and B Biol Sci. 2006; 361: 1565-1574 [PM: 16939975].
2. Benowitz L I, Yin Y. Combinatorial treatments for promoting axon regeneration in the CNS: strategies for overcoming inhibitory signals and activating neurons' intrinsic growth state. Dev Neurobiol 2007; 67:1148-1165. [PM: 17514713]
3. Nash M, Pribiag H, Fournier A E, Jacobson C. Central nervous system regeneration inhibitors and their intracellular substrates. Mol Neurobiol 2009; 40: 224-235. [PM: 19763907]
4. Raivich G, Makwana M. The making of successful axonal regeneration: genes, molecules and signal transduction pathways. Brain Res Rev 2007; 53: 287-311 [PM: 17079020].
5. Hanada M, Feng J, Hemmings B A. Structure, regulation and function of PKB/AKT—a major therapeutic target. Biochim Biophys Acta 2004; 1697: 3-16. [PM: 15023346].
6. Park, K K, Liu K, Hu Y, Smith P D, Wang C, Cai B, Xu B, Connolly L, Kramvis I, Sahin M, He Z., Promoting axon regeneration in the adult CNS by modulation of the PTEN/mTOR pathway. Science 2008: 322: 963-966. [PM: 18988856].
7. Liu K, Lu Y, Lee J K, Samara R, Willenberg R, Sears-Kraxberger I, Tedeschi A, Park K K, Jin D, Cai B, Xu B, Connolly L, Steward O, Zheng B, He Z. PTEN deletion enhances the regenerative ability of adult corticospinal neurons. Nat Neurosci 2010; 13: 1075-1081. [PM: 20594004].
8. Sauer H, Oertel W H. Progressive degeneration of nigrostriatal dopamine neurons following intrastriatal terminal lesions with 6 hydroxydopamine a combined retrograde tracing and immunocytochemical study in the rat. Neuroscience. 1994; 59: 401-415. [PM: 7516500].
9. Sato T, Umetsu A, Tamanoi F. Characterization of the Rheb-mTOR Signaling Pathway in Mammalian Cells: Constitutive Active Mutants of Rheb and mTOR. Methods Enzymol 2008; 438:307-320. [PM:18413257]
10. Zoncu R, Efeyan A, Sabatini D M. mTOR: from growth signal integration to cancer, diabetes and ageing. Nat Rev Mol Cell Biol 2011; 12:21-35. PM:21157483]
11. Kislauskis E H, Zhu X, Singer R H. Sequences responsible for intracellular localization of beta-actin messenger RNA also affect cell phenotype. J Cell Biol 1994; 127:441-451. [PM:7929587]
12. Bassell G J, Kelic S. Binding proteins for mRNA localization and local translation, and their dysfunction in genetic neurological disease. Curr Opin Neurobiol 2004; 14:574-581. [PM:15464890]
13. Huttelmaier S, Zenklusen D, Lederer M, Dictenberg J, Lorenz M, Meng X, Bassell G J, Condeelis J, Singer R H. Spatial regulation of beta-actin translation by Src-dependent phosphorylation of ZBP1. Nature 2005; 438:512-515. [PM:16306994]
14. Behar L, Marx R, Sadot E, Barg J, Ginzburg I. cis-acting signals and trans-acting proteins are involved in tau mRNA targeting into neurites of differentiating neuronal cells. Int J Dev Neurosci 1995; 13:113-127. [PM:7639096]
15. Aronov S, Aranda G, Behar L, Ginzburg I. Axonal tau mRNA localization coincides with tau protein in living neuronal cells and depends on axonal targeting signal. J Neurosci 2001; 21:6577-6587. [PM:11517247]
16. Satpute-Krishnan P, DeGiorgis J A, Conley M P, Jang M, Bearer E L. A peptide zip code sufficient for anterograde transport within amyloid precursor protein. Proc Natl Acad Sci USA 2006; 103:16532-16537. [PM:17062754]
17. Babetto E, Beirowski B, Janeckova L, Brown R, Gilley J, Thomson D, Ribchester R R, Coleman M P. Targeting NMNAT1 to axons and synapses transforms its neuroprotective potency in vivo. J Neurosci 2010; 30:13291-13304. PM:20926655]
18. Zuber M X, Strittmatter S M, Fishman M C. A membrane-targeting signal in the amino terminus of the neuronal protein GAP-43. Nature 1989; 341:345-348. [PM: 2797153].
19. Matsuda W, Furuta T, Nakamura K C, Hioki H, Fujiyama F, Arai R, Kaneko T. Single nigrostriatal dopaminergic neurons form widely spread and highly dense axonal arborizations in the neostriatum. J Neurosci 2009; 29:444-453. [PM:19144844].
20. Kim S R, Chen X, Oo T F, Kareva T, Yarygina O, Wang C, During M J, Kholodilov N, Burke R E (2011) Dopaminergic pathway reconstruction by Akt/Rheb-induced axon regeneration Ann Neurol 70 110-120.
21. Sun F, He Z. Neuronal intrinsic barriers for axon regeneration in the adult CNS. Curr Opin Neurobiol 2010; [PM: 20418094].
22. Hanada M, Feng J, Hemmings B A. Structure, regulation and function of PKB/AKT—a major therapeutic target. Biochim Biophys Acta 2004; 1697:3-16. [PM:15023346]
23. Ries V, Silva R M, Oo T F, Cheng H C, Rzhetskaya M, Kholodilov N, Flavell R A, Kuan C Y, Rakic P, Burke R E. JNK2 and JNK3 combined are essential for apoptosis in dopamine neurons of the substantia nigra, but are not required for axon degeneration. J Neurochem 2008; 107: 1578-1588. [PM:19014392]
24. Yan L, Findlay G M, Jones R, Procter J, Cao Y, Lamb R F. Hyperactivation of mammalian target of rapamycin (mTOR) signaling by a gain-of-function mutant of the Rheb GTPase. J Biol Chem 2006; 281:19793-19797. [PM: 16728407]
25. Sato T, Umetsu A, Tamanoi F. Characterization of the Rheb-mTOR Signaling Pathway in Mammalian Cells:

25. Constitutive Active Mutants of Rheb and mTOR. Methods Enzymol 2008; 438:307-320. [PM:18413257]
26. Zoncu R, Efeyan A, Sabatini D M. mTOR: from growth signal integration to cancer, diabetes and ageing. Nat Rev Mol Cell Biol 2011; 12:21-35. PM:21157483]
27. Kim S R, Chen X, Oo T F, Kareva T, Yarygina O, Wang C, During M J, Kholodilov N, Burke R E. Dopaminergic pathway reconstruction by Akt/Rheb-induced axon regeneration. Ann Neurol 2011; Huang J, Manning B D. A complex interplay between Akt, TSC2 and the two mTOR complexes. Biochem Soc Trans 2009; 37:217-222. [PM:19143635]
28. Choi Y J, Di Nardo A, Kramvis I, Meikle L, Kwiatkowski D J, Sahin M, He X. Tuberous sclerosis complex proteins control axon formation. Genes Dev 2008; 22:2485-2495. [PM:18794346]
29. Morita T, Sobue K. Specification of neuronal polarity regulated by local translation of CRMP2 and Tau via the mTOR-p70S6K pathway. J Biol Chem 009; 284:27734-27745. [PM:19648118]
30. Li Y H, Werner H, Puschel A W. Rheb and mTOR regulate neuronal polarity through Rap1B. J Biol Chem 2008; 283: 33784-33792. [PM:18842593]
31. Leung K M, van Horck F P, Lin A C, Allison R, Standart N, Holt C E. Asymmetrical beta-actin mRNA translation in growth cones mediates attractive turning to netrin-1. Nat Neurosci 2006; 9:1247-1256. [PM:16980963]
33. Job C, Eberwine J. Localization and translation of mRNA in dendrites and axons. Nat Rev Neurosci 2001; 2:889-898. [PM:11733796]
33. Holt C E, Bullock S L. Subcellular mRNA localization in animal cells and why it matters. Science 2009; 326:1212-1216. [PM:19965463]
34. Mayford M, Baranes D, Podsypanina K, Kandel E R. The 3'-untranslated region of CaMKII alpha is a cisacting signal for the localization and translation of mRNA in dendrites. Proc Natl Acad Sci USA 1996; 93:13250-13255. [PM:8917577]
35. Cheng H C, Kim S R, Oo T F, Kareva T, Yarygina O, Rzhetskaya M, Wang C, During M, Talloczy Z, Tanaka K, Komatsu M, Kobayashi K, Okano H, Kholodilov N, Burke R E. Akt suppresses retrograde degeneration of dopaminergic axons by inhibition of macroautophagy. J Neurosci 2011; 31:2125-2135. [PM:21307249]
36. Sauer H, Oertel W H. Progressive degeneration of nigrostriatal dopamine neurons following intrastriatal terminal lesions with 6 hydroxydopamine a combined retrograde tracing and immunocytochemical study in the rat. Neuroscience 1994; 59:401-415.
37. Silva R M, Ries V, Oo T F, Yarygina O, Jackson-Lewis V, Ryu E J, Lu P D, Marciniak S M, Ron D, Przedborski S, Kholodilov N, Greene L A, Burke R E. CHOP/GADD153 is a mediator of apoptotic death in substantia nigra dopamine neurons in an in vivo neurotoxin model of parkinsonism. J Neurochem 2005; 95:974-986. [PM:16135078]
38. Jefferies H B, Fumagalli S, Dennis P B, Reinhard C, Pearson R B, Thomas G. Rapamycin suppresses 5'TOP mRNA translation through inhibition of p70s6k. EMBO J 1997; 16:3693-3704. [PM:9218810]
39. Zhang W G, Shor B, Yu K. Identification and characterization of a constitutively T-loop phosphorylated and active recombinant S6K1: expression, purification, and enzymatic studies in a high capacity non-radioactive TR-FRET Lance assay. Protein Expr Purif 2006; 46:414-420. [PM:16213157]
40. Elghazi L, Balcazar N, Blandino-Rosano M, Cras-Meneur C, Fatrai S, Gould A P, Chi M M, Moley K H, Bernal-Mizrachi E. Decreased IRS signaling impairs beta-cell cycle progression and survival in transgenic mice overexpressing S6K in beta-cells. Diabetes 2010; 59:2390-2399. [PM:20622167]
41. Stettler O, Bush M S, Kasper M, Schlosshauer B, Gordon-Weeks P R. Monoclonal antibody 2G13, a new axonal growth cone marker. J Neurocytol 1999; 28:1035-1044. [PM:11054903]
42. Maier I C, Baumann K, Thallmair M, Weinmann O, Scholl J, Schwab M E. Constraint-induced movement therapy in the adult rat after unilateral corticospinal tract injury. J Neurosci 2008; 28:9386-9403. [PM:18799672]
43. Chen X, Rzhetskaya M, Kareva T, Bland R, During M J, Tank A W, Kholodilov N, Burke R E. Antiapoptotic and trophic effects of dominant-negative forms of dual leucine zipper kinase in dopamine neurons of the substantia nigra in vivo. J Neurosci 2008; 28:672-680. [PM:18199767]
44. Olson V G, Heusner C L, Bland R J, During M J, Weinshenker D, Palmiter R D. Role of noradrenergic signaling by the nucleus tractus solitarius in mediating opiate reward. Science 2006; 311:1017-1020. [PM:16484499]
45. Kholodilov N, Yarygina O, Oo T F, Zhang H, Sulzer D, Dauer W T, Burke R E. Regulation of the development of mesencephalic dopaminergic systems by the selective expression of glial cell linederived neurotrophic factor in their targets. J Neurosci 2004; 24:3136-3146.
46. Sawamoto K, Nakao N, Kobayashi K, Matsushita N, Takahashi H, Kakishita K, Yamamoto A, Yoshizaki T, Terashima T, Murakami F, Itakura T, Okano H. Visualization, direct isolation, and transplantation of midbrain dopaminergic neurons. Proc Natl Acad Sci USA 2001; 98:6423-6428. [PM:11353855]
47. Cheng H C, Burke R E. The Wld(S) mutation delays anterograde, but not retrograde, axonal degeneration of the dopaminergic nigro-striatal pathway in vivo. J Neurochem 2010; 113:683-691. [PM:20132467]
48. Montanaro L, Pandolfi P P. Initiation of mRNA translation in oncogenesis: the role of eIF4E. Cell Cycle 2004; 3:1387-1389. [PM:15492504]
49. Goodfellow I G, Roberts L O. Eukaryotic initiation factor 4E. Int J Biochem Cell Biol 2008; 40:2675-2680. [PM:18069043]
50. Lachance P E, Miron M, Raught B, Sonenberg N, Lasko P. Phosphorylation of eukaryotic translation initiation factor 4E is critical for growth. Mol Cell Biol 2002; 22:1656-1663. [PM:11865045]
51. Ruggero D, Montanaro L, Ma L, Xu W, Londei P, Cordon-Cardo C, Pandolfi P P. The translation factor eIF-4E promotes tumor formation and cooperates with c-Myc in lymphomagenesis. Nat Med 2004; 10:484-486. [PM:15098029]
52. Wendel H G, De Stanchina E, Fridman J S, Malina A, Ray S, Kogan S, Cordon-Cardo C, Pelletier J, Lowe S W. Survival signalling by Akt and eIF4E in oncogenesis and cancer therapy. Nature 2004; 428:332-337. [PM:15029198]
53. Dowling R J, Topisirovic I, Alain T, Bidinosti M, Fonseca B D, Petroulakis E, Wang X, Larsson O, Selvaraj A, Liu Y, Kozma S C, Thomas G, Sonenberg N. mTORC1-mediated cell proliferation, but not cell growth, controlled by the 4E-BPs. Science 2010; 328:1172-1176. [PM:20508131]
54. Li Y, Liu W, Oo T F, Wang L, Tang Y, Jackson-Lewis V, Zhou C, Geghman K, Bogdanov M, Przedborski S, Beal M F, Burke R E, Li C. Mutant LRRK2(R1441G) BAC transgenic mice recapitulate cardinal features of Parkinson's disease. Nat Neurosci 2009; 12:826-828. [PM:19503083]

55. Paisan-Ruiz C, Jain S, Evans E W, Gilks W P, Simon J, van der B M, Lopez d M, Aparicio S, Gil A M, Khan N, Johnson J, Martinez J R, Nicholl D, Carrera I M, Pena A S, de Silva R, Lees A, Marti-Masso J F, Perez-Tur J, Wood N W, Singleton A B. Cloning of the gene containing mutations that cause PARK8-linked Parkinson's disease. Neuron 2004; 44:595-600. [PM:15541308]

56. Zimprich A, Biskup S, Leitner P, Lichtner P, Farrer M, Lincoln S, Kachergus J, Hulihan M, Uitti R J, Calne D B, Stoessl A J, Pfeiffer R F, Patenge N, Carbajal I C, Vieregge P, Asmus F, Muller-Myhsok B, Dickson D W, Meitinger T, Strom T M, Wszolek Z K, Gasser T. Mutations in LRRK2 cause autosomal-dominant parkinsonism with pleomorphic pathology. Neuron 2004; 44:601-607. [PM:15541309]

What is claimed is:

1. A gene delivery vehicle comprising
   (a) a gene hp70S6K (CA) identified by SEQ ID NO. 1 that encodes a constitutively active form of protein hp70S6K (delC/T389E) identified by SEQ ID NO. 2; and
   (b) a 3' UTR zip code or a short peptide sequence zip code that targets neurons.

2. The gene delivery vehicle of claim 1, wherein the vehicle is a viral construct.

3. The viral construct of claim 2, further comprising:
   (c) a chicken β-actin (CBA) promoter;
   (d) the gene hp70S6K (CA) identified by SEQ ID NO. 1, encoding a constitutively active form of protein hp70S6K (delC/T389E) identified by SEQ ID NO. 2, located downstream of the chicken β-actin promoter;
   (e) a 3' woodchuck post-transcriptional regulatory element WPRE (pBL)) located downstream of the gene; and
   (f) a bovine growth hormone polyadenylation sequence (BGHpolyA) inserted before a 3' inverted terminal repeat (ITR) sequence.

4. The viral construct of claim 1 wherein the short peptide sequence zip code is identified by SEQ ID NO.: 3.

5. The viral construct of claim 2, wherein the viral construct is an adeno-associated construct.

6. The adeno-associated construct of claim 5, comprising a serotype selected from the group consisting of AAV-1, AAV-2, AAV-3, AAV-4, AAV-5, AAV-6, AAV-9, AAV-10, and AAV-11.

7. A pharmaceutical composition comprising the viral construct of claim 2.

8. A kit comprising the pharmaceutical composition of claim 7.

9. An AAV1 viral construct comprising (a) a gene hp70S6K (CA) identified by SEQ ID NO. 1 that encodes a constitutively active form of protein hp70S6K (delC/T389E) identified by SEQ ID NO. 2; and
   (b) a 3' UTR zip code or a short peptide sequence zip code that targets neurons.

* * * * *

SEQUENCE LISTING

```
<160> NUMBER OF SEQ ID NOS: 3

<210> SEQ ID NO 1
<211> LENGTH: 1197
<212> TYPE: DNA
<213> ORGANISM: Artificial Sequence
<220> FEATURE:
<223> OTHER INFORMATION: Synthetic construct: hp70S6K(CA) DNA sequence

<400> SEQUENCE: 1
atggcaggag tgtttgacat agacctggac cagccagagg acgcgggctc tgaggatgag      60
ctggaggagg ggggtcagtt aaatgaaagc atggaccatg ggggagttgg accatatgaa     120
cttggcatgg aacattgtga gaaatttgaa atctcagaaa ctagtgtgaa cagagggcca     180
gaaaaaatca gaccagaatg ttttgagcta cttcgggtac ttggtaaagg gggctatgga     240
aaggtttttc aagtacgaaa agtaacagga gcaaatactg ggaaaatatt tgccatgaag     300
gtgcttaaaa aggcaatgat agtaagaaat gctaaagata cagctcatac aaaagcagaa     360
cggaatattc tggaggaagt aaagcatccc ttcatcgtgg atttaattta tgcctttcag     420
actggtggaa aactctacct catccttgag tatctcagtg gaggagaact atttatgcag     480
ttagaaagag agggaatatt tatggaagac actgcctgct tttacttggc agaaatctcc     540
atggctttgg ggcatttaca tcaaaagggg atcatctaca gagacctgaa gccggagaat     600
atcatgctta atcaccaagg tcatgtgaaa ctaacagact ttggactatg caaagaatct     660
attcatgatg aacagtcac acacacattt tgtggaacaa tagaatacat ggcccctgaa      720
atcttgatga gaagtggcca aatcgtgct gtggattggt ggagtttggg agcattaatg     780
tatgacatgc tgactggagc accccattc actggggaga atagaaagaa aacaattgac     840
aaaatcctca aatgtaaact caatttgcct ccctacctca cacaagaagc cagagatctg     900
cttaaaaagc tgctgaaaag aaatgctgct tctcgtctgg gagctggtcc tggggacgct     960
ggagaagttc aagctcatcc attctttaga cacattaact gggaagaact tctggctcga    1020
aaggtggagc cccccttaa acctctgttg caatctgaag aggatgtaag tcagtttgat     1080
tccaagttta cacgtcagac acctgtcgac agcccagatg actcaactct cagtgaaagt     1140
gccaatcagg tcttcctggg ttttgaatat gtggctccat ctgtacttga aagttaa        1197

<210> SEQ ID NO 2
<211> LENGTH: 398
<212> TYPE: PRT
<213> ORGANISM: Artificial Sequence
<220> FEATURE:
<223> OTHER INFORMATION: Synthetic construct: hp70S6K (delC/T389E)
      protein sequence

<400> SEQUENCE: 2

Met Ala Gly Val Phe Asp Ile Asp Leu Asp Gln Pro Glu Asp Ala Gly
  1               5                  10                  15

Ser Glu Asp Glu Leu Glu Glu Gly Gly Gln Leu Asn Glu Ser Met Asp
```

```
            20                  25                  30
His Gly Gly Val Gly Pro Tyr Glu Leu Gly Met Glu His Cys Glu Lys
                35                  40                  45
Phe Glu Ile Ser Glu Thr Ser Val Asn Arg Gly Pro Glu Lys Ile Arg
        50                  55                  60
Pro Glu Cys Phe Glu Leu Leu Arg Val Leu Gly Lys Gly Gly Tyr Gly
65                  70                  75                  80
Lys Val Phe Gln Val Arg Lys Val Thr Gly Ala Asn Thr Gly Lys Ile
                85                  90                  95
Phe Ala Met Lys Val Leu Lys Lys Ala Met Ile Val Arg Asn Ala Lys
                100                 105                 110
Asp Thr Ala His Thr Lys Ala Glu Arg Asn Ile Leu Glu Glu Val Lys
                115                 120                 125
His Pro Phe Ile Val Asp Leu Ile Tyr Ala Phe Gln Thr Gly Gly Lys
                130                 135                 140
Leu Tyr Leu Ile Leu Glu Tyr Leu Ser Gly Gly Glu Leu Phe Met Gln
145                 150                 155                 160
Leu Glu Arg Glu Gly Ile Phe Met Glu Asp Thr Ala Cys Phe Tyr Leu
                165                 170                 175
Ala Glu Ile Ser Met Ala Leu Gly His Leu His Gln Lys Gly Ile Ile
                180                 185                 190
Tyr Arg Asp Leu Lys Pro Glu Asn Ile Met Leu Asn His Gln Gly His
                195                 200                 205
Val Lys Leu Thr Asp Phe Gly Leu Cys Lys Glu Ser Ile His Asp Gly
                210                 215                 220
Thr Val Thr His Thr Phe Cys Gly Thr Ile Glu Tyr Met Ala Pro Glu
225                 230                 235                 240
Ile Leu Met Arg Ser Gly His Asn Arg Ala Val Asp Trp Trp Ser Leu
                245                 250                 255
Gly Ala Leu Met Tyr Asp Met Leu Thr Gly Ala Pro Pro Phe Thr Gly
                260                 265                 270
Glu Asn Arg Lys Lys Thr Ile Asp Lys Ile Leu Lys Cys Lys Leu Asn
                275                 280                 285
Leu Pro Pro Tyr Leu Thr Gln Glu Ala Arg Asp Leu Leu Lys Lys Leu
                290                 295                 300
Leu Lys Arg Asn Ala Ala Ser Arg Leu Gly Ala Gly Pro Gly Asp Ala
305                 310                 315                 320
Gly Glu Val Gln Ala His Pro Phe Phe Arg His Ile Asn Trp Glu Glu
                325                 330                 335
Leu Leu Ala Arg Lys Val Glu Pro Pro Phe Lys Pro Leu Leu Gln Ser
                340                 345                 350
Glu Glu Asp Val Ser Gln Phe Asp Ser Lys Phe Thr Arg Gln Thr Pro
                355                 360                 365
Val Asp Ser Pro Asp Asp Ser Thr Leu Ser Glu Ser Ala Asn Gln Val
                370                 375                 380
Phe Leu Gly Phe Glu Tyr Val Ala Pro Ser Val Leu Glu Ser
385                 390                 395

<210> SEQ ID NO 3
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 3

Gly Tyr Glu Asn Pro Thr Tyr Lys Phe Phe Glu Gln Met Gln Asn
1               5                   10                  15
```